(12) United States Patent
Jensen et al.

(10) Patent No.: US 11,033,499 B2
(45) Date of Patent: *Jun. 15, 2021

(54) TABLET FORMULATION COMPRISING A GLP-1 PEPTIDE AND A DELIVERY AGENT

(71) Applicant: Novo Nordisk A/S, Bagsvaerd (DK)

(72) Inventors: Simon Bjerregaard Jensen, Hilleroed (DK); Per Sauerberg, Farum (DK); Flemming S. Nielsen, Roskilde (DK); Betty L. Pedersen, Glostrup (DK); Erik Skibsted, Hollbaek (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/958,236

(22) Filed: Apr. 20, 2018

(65) Prior Publication Data

US 2018/0235888 A1    Aug. 23, 2018

Related U.S. Application Data

(63) Continuation of application No. 14/409,021, filed as application No. PCT/EP2013/062751 on Jun. 19, 2013, now Pat. No. 9,993,430.

(60) Provisional application No. 61/662,456, filed on Jun. 21, 2012.

(30) Foreign Application Priority Data

Jun. 20, 2012 (EP) .................................... 12172739

(51) Int. Cl.
| | |
|---|---|
| *A61K 9/20* | (2006.01) |
| *A61K 9/26* | (2006.01) |
| *A61K 38/26* | (2006.01) |
| *A61K 9/16* | (2006.01) |

(52) U.S. Cl.
CPC .......... *A61K 9/2013* (2013.01); *A61K 9/1617* (2013.01); *A61K 9/2004* (2013.01); *A61K 9/2072* (2013.01); *A61K 9/2077* (2013.01); *A61K 9/2095* (2013.01); *A61K 38/26* (2013.01)

(58) Field of Classification Search
None
See application file for complete search history.

(56) References Cited

U.S. PATENT DOCUMENTS

| | | | |
|---|---|---|---|
| 5,545,618 A | 8/1996 | Buckley et al. | |
| 5,773,647 A | 6/1998 | Leone-Bay et al. | |
| 5,866,536 A | 2/1999 | Leone-Bay et al. | |
| 5,968,899 A | 10/1999 | Sekine et al. | |
| 6,268,343 B1 | 7/2001 | Knudsen et al. | |
| 6,458,924 B2 | 10/2002 | Knudsen et al. | |
| 7,049,283 B2 | 5/2006 | Ault et al. | |
| 7,235,627 B2 | 6/2007 | Knudson et al. | |
| 7,271,149 B2 | 9/2007 | Glaesner et al. | |
| 8,039,018 B2 | 10/2011 | Majuru et al. | |
| 8,053,429 B2 | 11/2011 | Cumming et al. | |
| 8,097,698 B2 | 1/2012 | Knudsen et al. | |
| 8,536,122 B2 | 9/2013 | Lau et al. | |
| 8,648,041 B2 | 2/2014 | Garibay et al. | |
| 8,895,694 B2 | 11/2014 | Spetzler et al. | |
| 9,067,977 B2 | 6/2015 | Spetzler et al. | |
| 9,266,940 B2 | 2/2016 | Wieczorek et al. | |
| 9,278,123 B2 | 3/2016 | Sauerberg et al. | |
| 9,527,900 B2 | 12/2016 | Linderoth et al. | |
| 9,993,430 B2 | 6/2018 | Jensen et al. | |
| 10,005,827 B2 | 6/2018 | Spetzler et al. | |
| 10,278,923 B2 | 5/2019 | Nielsen et al. | |
| 2001/0011071 A1 | 8/2001 | Knudsen et al. | |
| 2005/0009748 A1 | 1/2005 | Dinh et al. | |
| 2005/0148497 A1 | 7/2005 | Khan | |
| 2006/0078622 A1 | 4/2006 | Majuru et al. | |
| 2006/0286129 A1 | 12/2006 | Sarubbi | |
| 2007/0049557 A1 | 3/2007 | Ahmed et al. | |
| 2007/0203058 A1 | 8/2007 | Lau et al. | |
| 2007/0224262 A1 | 9/2007 | Majuru et al. | |
| 2008/0076705 A1 | 3/2008 | Kodra et al. | |
| 2008/0153779 A1 | 6/2008 | Liao et al. | |
| 2008/0194676 A1 | 8/2008 | Abbas et al. | |
| 2008/0207507 A1 | 8/2008 | Lau et al. | |
| 2008/0255250 A1 | 10/2008 | Gomez-Orellana et al. | |
| 2009/0088369 A1 | 4/2009 | Steiness | |
| 2009/0124639 A1 | 5/2009 | Oyewumi et al. | |
| 2009/0143330 A1* | 6/2009 | Levchik ............... | A61K 9/0053 514/56 |
| 2009/0156478 A1 | 6/2009 | Lau et al. | |
| 2010/0016229 A1 | 1/2010 | Sarubbi | |
| 2010/0069410 A1 | 3/2010 | Majuru et al. | |
| 2010/0151009 A1 | 6/2010 | Levchik | |
| 2010/0210526 A1 | 8/2010 | Joshi | |

(Continued)

FOREIGN PATENT DOCUMENTS

| | | |
|---|---|---|
| CN | 101010339 A | 8/2007 |
| CN | 101133082 A | 2/2008 |
| CN | 101463081 A | 6/2009 |
| EP | 0708179 A2 | 4/1996 |
| EP | 1364967 A2 | 11/2003 |
| EP | 2565202 A1 | 3/2013 |
| EP | 2651398 A1 | 10/2013 |
| JP | 05-506427 | 9/1993 |
| JP | H05-506427 A | 9/1993 |
| JP | 2001-504105 A | 3/2001 |
| JP | 2004131398 A | 4/2004 |
| JP | 2006-520818 A | 9/2006 |
| JP | 2007-536268 A | 12/2007 |
| JP | 2008-509933 A | 4/2008 |

(Continued)

OTHER PUBLICATIONS

Wang et al., "Non-peptidic glucose-like peptide-1 receptor agonists: aftermath of serendipitous discovery," Acta Pharmacol. Sinica, 2010, vol. 31, pp. 1026-1030.

(Continued)

*Primary Examiner* — Kevin S Orwig
(74) *Attorney, Agent, or Firm* — Leon Y. Lum

(57) ABSTRACT

The present invention relates to solid compositions comprising a GLP-1 peptide and a delivery agent, such as SNAC, as well as uses thereof.

16 Claims, 6 Drawing Sheets

Specification includes a Sequence Listing.

(56) References Cited

U.S. PATENT DOCUMENTS

| | | |
|---|---|---|
| 2010/0239658 A1 | 9/2010 | Majuru et al. |
| 2010/0292133 A1 | 11/2010 | Spetzler et al. |
| 2011/0142800 A1 | 6/2011 | Kidron et al. |
| 2011/0166321 A1 | 7/2011 | Garibay et al. |
| 2011/0218148 A1 | 9/2011 | Azria et al. |
| 2013/0053311 A1 | 2/2013 | Kalthoff et al. |
| 2013/0345134 A1 | 12/2013 | Sauerberg et al. |
| 2014/0011732 A1 | 1/2014 | Spetzler et al. |
| 2014/0296131 A1 | 10/2014 | Spetzler et al. |
| 2015/0025003 A1 | 1/2015 | Spetzler et al. |
| 2015/0031606 A1 | 1/2015 | Vilhelmsen |
| 2015/0072926 A1 | 3/2015 | Vilhelmsen et al. |
| 2016/0067184 A1 | 3/2016 | Nielsen et al. |
| 2016/0151462 A1 | 6/2016 | Sauerberg et al. |
| 2017/0312225 A1 | 11/2017 | Nielsen et al. |
| 2018/0021272 A1 | 1/2018 | Burshtein et al. |
| 2018/0028622 A1 | 2/2018 | Burshtein et al. |
| 2018/0036234 A1 | 2/2018 | Burshtein et al. |
| 2018/0036382 A1 | 2/2018 | Burshtein et al. |
| 2018/0050096 A1 | 2/2018 | Burshtein et al. |
| 2018/0235888 A1 | 8/2018 | Jensen et al. |
| 2018/0251512 A1 | 9/2018 | Wieczorek et al. |
| 2018/0360918 A1 | 12/2018 | Sauerberg et al. |
| 2019/0216739 A1 | 7/2019 | Nielsen et al. |
| 2019/0231876 A1 | 8/2019 | Pedersen et al. |
| 2019/0314283 A1 | 10/2019 | Vilhelmsen |
| 2020/0079834 A1 | 3/2020 | Wieczorek et al. |

FOREIGN PATENT DOCUMENTS

| | | |
|---|---|---|
| JP | 2009542711 A | 12/2009 |
| JP | 2010-530962 A | 9/2010 |
| JP | 4585037 B2 | 11/2010 |
| JP | 2011509077 A | 3/2011 |
| JP | 2012-121923 A | 6/2012 |
| JP | 2013543814 A | 12/2013 |
| JP | 2014503526 A | 2/2014 |
| JP | 2015-515459 A | 5/2015 |
| KR | 20060100428 A | 9/2006 |
| KR | 102072202 | 1/2020 |
| NZ | 219575 A | 4/1990 |
| RU | 2158138 C2 | 10/2000 |
| RU | 2226402 C2 | 4/2004 |
| WO | 9111457 A1 | 8/1991 |
| WO | 96/29342 | 9/1996 |
| WO | 98/08871 A1 | 3/1998 |
| WO | 9820895 A1 | 5/1998 |
| WO | 99/43705 A1 | 9/1999 |
| WO | 99/43706 A1 | 9/1999 |
| WO | 99/43707 A1 | 9/1999 |
| WO | 99/43708 A1 | 9/1999 |
| WO | 00/07617 A1 | 2/2000 |
| WO | 00/16797 A2 | 3/2000 |
| WO | 00/34331 | 6/2000 |
| WO | 200048589 A1 | 8/2000 |
| WO | 200050012 A1 | 8/2000 |
| WO | 00/69911 | 11/2000 |
| WO | 0066629 A1 | 11/2000 |
| WO | 01/04156 | 1/2001 |
| WO | 0124777 A1 | 4/2001 |
| WO | 200141737 A2 | 6/2001 |
| WO | 02/46227 A2 | 6/2002 |
| WO | 0248192 A2 | 6/2002 |
| WO | 2003005944 A1 | 1/2003 |
| WO | 03/011892 A2 | 2/2003 |
| WO | 03063838 A1 | 8/2003 |
| WO | 03/072195 A2 | 9/2003 |
| WO | 2004/067548 A2 | 8/2004 |
| WO | 2004093823 A2 | 11/2004 |
| WO | 2005004900 A1 | 1/2005 |
| WO | 2005/014035 A2 | 2/2005 |
| WO | 2005014049 A2 | 2/2005 |
| WO | 2005/027978 A2 | 3/2005 |
| WO | 2005/058954 A1 | 6/2005 |
| WO | 2005/058958 A2 | 6/2005 |
| WO | 2005049061 A2 | 6/2005 |
| WO | 2005099672 A1 | 10/2005 |
| WO | 2005107462 A2 | 11/2005 |
| WO | 2005107773 A2 | 11/2005 |
| WO | 2005/121090 A1 | 12/2005 |
| WO | 2006/005667 A2 | 1/2006 |
| WO | 2006/037810 | 4/2006 |
| WO | 2006/082204 A1 | 8/2006 |
| WO | 2006084164 A2 | 8/2006 |
| WO | 2006/097535 A2 | 9/2006 |
| WO | 2006/097536 A2 | 9/2006 |
| WO | 2006/097537 A2 | 9/2006 |
| WO | 2006/097538 | 9/2006 |
| WO | 2006/097538 A1 | 9/2006 |
| WO | 2006096515 A2 | 9/2006 |
| WO | 2006097537 A2 | 9/2006 |
| WO | 2006103661 A2 | 10/2006 |
| WO | 2006/127948 A2 | 11/2006 |
| WO | 2006124047 A2 | 11/2006 |
| WO | 2007024700 A2 | 3/2007 |
| WO | 2007061434 A2 | 5/2007 |
| WO | 2007067964 A2 | 6/2007 |
| WO | 2007093226 A1 | 8/2007 |
| WO | 2007117706 A2 | 10/2007 |
| WO | 2007/128817 A2 | 11/2007 |
| WO | 2007146234 A2 | 12/2007 |
| WO | 2008003050 A2 | 1/2008 |
| WO | 2008020096 A1 | 2/2008 |
| WO | 2008028859 A1 | 3/2008 |
| WO | 2008033888 A2 | 3/2008 |
| WO | 2008039351 A2 | 4/2008 |
| WO | 2008109385 A2 | 9/2008 |
| WO | 2008/154619 A1 | 12/2008 |
| WO | 2009/030771 A1 | 3/2009 |
| WO | 2009030738 A1 | 3/2009 |
| WO | 2009032749 A2 | 3/2009 |
| WO | 2009/050738 A2 | 4/2009 |
| WO | 2009059188 A1 | 5/2009 |
| WO | 2009/083549 A1 | 7/2009 |
| WO | 2010/020978 A1 | 2/2010 |
| WO | 2010020978 A1 | 2/2010 |
| WO | 2010/029159 A1 | 3/2010 |
| WO | 2010/043319 A1 | 4/2010 |
| WO | 2010/092163 A2 | 8/2010 |
| WO | 2011/029551 A2 | 3/2011 |
| WO | 2011084618 A2 | 7/2011 |
| WO | 2011094531 A1 | 8/2011 |
| WO | 2011109787 A1 | 9/2011 |
| WO | 2011116139 A2 | 9/2011 |
| WO | 2011138421 A1 | 11/2011 |
| WO | 2012080471 A1 | 6/2012 |
| WO | 2012140117 A1 | 10/2012 |
| WO | 2013009545 A1 | 1/2013 |
| WO | 2013139694 | 9/2013 |
| WO | 2013139694 A1 | 9/2013 |
| WO | 2013139695 A1 | 9/2013 |
| WO | 2013189988 A1 | 12/2013 |
| WO | 2014005858 A1 | 1/2014 |
| WO | 2014177683 A1 | 11/2014 |
| WO | 2016128970 A1 | 8/2016 |
| WO | 2016128971 A1 | 8/2016 |
| WO | 2016128972 A1 | 8/2016 |
| WO | 2016128973 A1 | 8/2016 |
| WO | 2016128974 A1 | 8/2016 |
| WO | 2017060500 A1 | 4/2017 |

OTHER PUBLICATIONS

Bastin et al., "Salt Selection and Optimisation Procedures for Pharmaceutical New Chemical Entities," Org Proc Res & Devt, 2000, vol. 4, pp. 427-435.
Drug Data Report, 2006, vol. 28, p. 933.
Keck et al., Moderne Pharmazeutische Technologie, 2009, pp. 8-14.
Kidron et al., "A Novel Per-Oral Insulin Formulation: Proof of Concept Study in Non-Diabetic Subjects," Diabetic Medicine, 2004, vol. 21, pp. 354-357.
Letter to Sandoz International GmbH regarding English translation of claim of patent JP4585037, dated Aug. 29, 2018.

(56) References Cited

OTHER PUBLICATIONS

Mullins, "Statistics for the Quality Control Chemistry Laboratory," 2003, Chapter I, pp. 10-17.
Valentino et al., "Current Trends in Targeting the Hormonal Regulation of Appetite and Energy Balance to Treat Obesity," Expert Rev Endocrinol Metab, 2010, vol. 5, pp. 765-783.
WHO Drug Information, "International Nonproprietary Names for Pharmaceutical Substances," 2009, vol. 23, No. 2, p. 164.
U.S. Appl. No. 61/425,087, filed Dec. 20, 2010.
EP Application No. 10195285.1, filed Dec. 16, 2010.
Antony J Hickey et al., Pharmaceutical Process Engineering (Second edition) (2010) p. 159.
Bruce J. Aungst, "Absorption enhancers: applications and advances," The MPS Journal, 2011, vol. 14, No. 1, pp. 10-18.
Diabetes Close Up, Baby Steps, Mar./Apr. 2011, No. 106, pp. 1-50.
Dilip M. Parikh, Handbook of Pharmaceutical Granulation Technology (Second edition) (2005), Process-related variables, p. 7, p. 10-14 and p. 330.
EP Application 12160743, filed Mar. 22, 2012.
EP Application 13153459, filed Jan. 31, 2013.
Handbook of Pharmaceutical Granulation Technology, Second Edition, 2005, vol. 154, Introduction, pp. 1-6.
R. F. Witkamp, "Current and Future Drug Targets in Weight Management," Pharm Res, 2011, vol. 28, pp. 1792-1818.
Salem et al., "Approaches to the pharmacological treatment of obesity," Expert Rev Clin Pharmacol, 2010, vol. 3, No. 1, pp. 73-88.
The Handbook of Powder Technology "Granulation", vol. 11, 2006, p. 1190.
U.S. Appl. No. 61/748,840, filed Jan. 4, 2013.
Beglinger C et al., Clinical Pharmacology and Therapeutics,"Pharmacokinetics and Pharmacodynamic Effects of Oral GLP-1 and PYY3-36: A Proof-Of-Concept Study in Healthy Subjects"., 2008, vol. 84, No. 4, pp. 468-474.
Steinert RE et al, American Journal of Clinical Nutrition,"Oral Administration of Glucagon-Like Peptide 1 or Peptide YY 3-36 Affects Food Intake in Healthy Male Subjects", 2010, vol. 92, pp. 810-817.
He Xiaorong et al., Mechanistic Study of the Effect of Roller Compaction and Lubricant on Tablet Mechanical Strength, Journal: Journal of Pharmaceutical Sciences,Year: 2007, vol. 96, No. 5, pp. 1342-1355.
Mollan Jr. Matthew J. et al., The effects of lubrication on the compaction and post-compaction properties of directly compressible maltodextrins, Journal: International Journal of Pharmaceutics, Year: 1996, vol. 144, Issue 1, pp. 1-9.
Rowe Raymond C et al., Book: Handbook of Pharmaceutical Excipients, Title: Acesulfame Potassium, Edition—5th, Year: 2006, Complete book.
Steinert R E et al., Orally Administered Glucagon-Like Peptide-1 Affects Glucose Homeostasis Following an Oral Glucose Tolerance Test in Healthy Male Subjects, Journal: Clinical Pharmacology and Therapeutics, Year: 2009, vol. 86, No. 6, pp. 644-650.
Von Eggelkraut-Gottanka Stephan G. et al., Roller Compaction and Tabletting of St. John's Wort Plant Dry Extract Using a Gap Width and Force Controlled Roller; Compactor. II. Study of Roller Compaction Variables on Granule and Tablet Properties by a 33 Factorial Design, Journal: Pharmaceutical Development and Technology, Year: 2002, vol. 7, No. 4, pp. 447-455.
Beglinger C et al., Pharmacokinetics and Pharmacodynamic Effects of Oral GLP-1 and PYY3-36: A Proof-of-concept Study in Healthy Subjects, Journal: Clinical Pharmacology & Therapeutics, Nature Publishing Group, Year: 2008. vol. 84, No. 4, pp. 468-474.
Leonard Thomas W et al., Promoting absorption of drugs in humans using medium-chain fatty acid-based solid dosage forms:GIPET™, Journal: Expert Opinion Drug Delivery, Year: 2006, vol. 3(5), pp. 685-692.
Maher Sam et al., Overcoming poor permeability: translating permeation enhancers for oral peptide delivery, Journal: Drug Discovery Today:Technologies, Year: 2011, vol. 9, No. 2, pp. e113-e119.

Maher Sam et al., Safety and efficacy of sodium caprate in promoting oral drug absorption: from in vitro to the clinic, Journal: Advanced Drug Delivery Reviews, Year: 2009, vol. 61, pp. 1427-1449.
Michel Marre et al., GLP-1 receptor agonists today, Journal: Diabetes Research; and Clinical Practice, Year: 2011, vol. 93, No. 3, pp. 317-327.
Walsch Edwin G et al., Oral delivery of macromolecules: rationale underpinning Gastrointestinal Permeation Enhancement Technology (GIPET®), Journal: Therapeutic Delivery, Year: 2011, vol. 2, No. 12, pp. 1595-1610. OTH.
Makoto Otsuka, Chemoinformetrical evaluation of granule and tablet properties of pharmaceutical preparations by near-infrared spectroscopy, "Chemometrics and Intelligent Laboratory Systems" Year 2006, vol. 82, No. 1-2, pp. 109-114.
Shah R. B et al. Process Analytical Technology: Chemometric Analysis of Raman and Near Infra-red Spectroscopic Data for Predicting Physical Properties of Extended Release Matrix Tablets, "Journal of Pharmaceutical Sciences" Year 2007, vol. 96, No. 5, pp. 1356-1365.
Aenugu H.P.R et al. Near Infra Red Spectroscopy—An Overview, "International Journal of ChemTech Research" Year 2011, vol. 3, No. 2, pp. 825-836.
Donoso M et al. Prediction of Tablet Hardness and Porosity Using Near-Infrared Diffuse Reflectance Spectroscopy as a Nondestructive Method, "Pharmaceutical Development and Technology" Year 2003, vol. 8, No. 4, pp. 357-366.
Jeckel et al. Importance of particle size knowledge for tablet porosity determination by NIRS, "Tablet Tech Seminar, FMC Biopolymer" Year 2007, retrieved from the Internet: URL:http://www.pharmtech.uni-bonn.de/forschung/arbeitskreis-port-steffens/download-16, the whole document.
Remington, The Science and Practice of Pharmacy, 22nd Edition, 2012.
Felix Kratz "A Clinical Update of Using Albumin as a Drug Vehicle—A Commentary" Journal of Controlled Release 2014 vol. 190 pp. 331-336.
Rivera et al. Oral Delivery of Heparin in Combination with Sodium N-[8-(2-Hydroxybenzoyl)amino]caprylate: Pharmacological Considerations. Pharmaceutical Research 1997 vol. 14 No. 12 pp. 1830-1834.
Su Young Chae et al. "Preparation, Characterization and Application of Biotinylated and Biotin-PEGylated Glucagon-Like Peptide-1 Analogues for Enhanced Oral Delivery." Bioconjugate Chemistry 2008 vol. 19 No. 1 pp. 334-341.
Emisphere Technologies. "Carriers Enhance Drug Delivery" Manufacturing Chemistry 1999 vol. 70 No. 6 pp. 25-26.
Adam W. G. Alani et al., "Mechanistic Understanding of Oral Drug Absorption Enhancement of Cromolyn Sodium by an Amino Acid Derivative," Pharmaceutical Research, 2008, vol. 25, No. 1, pp. 48-54.
Bhansali et al., "Historical Overview of Incretin Based Therapies," Supplement to JAPI, 2010, vol. 58, pp. 10-14.
Valentino et al., "Central and Peripheral Molecular Targets for Antiobesity Pharmacotherapy," Clinical Pharmacology and Therapeutics, 2010, vol. 87, No. 6, pp. 652-662.
Baynes, Kevin C. R., "The evolving world of GLP-1 agonist therapies for type 2 diabetes" Therapeutic Advances in Endocnnology and Metabolism, 2010,,vol. 1, No. 2, pp. 61-67.
Buckley, Stephen T. et al., "Transcellular stomach absorption of a derivatized glucagon-like peptide-1 receptor agonist" Science Translational Medicine, Nov. 14, 2018, vol. 10, pp. 1-14.
Christensen, Mikkel et al., "Once-Weekly GLP-1 Agonists: How Do They Differ from Exenatide and Liraglutide?" Curr Diab Rep, 2010, vol. 10, pp. 124-132.
Davies, Melanie et al., "Effect of Oral Semaglutide Compared with Placebo and Subcutaneous Semaglutide on Glycemic Control in Patients with Type 2 Diabetes" JAMA, 2017, vol. 318, pp. 1460-1470.
Declaration by the Inventor, Flemming S. Nielsen, dated Feb. 11, 2019.
EMEA Assessment Report EMEA/37917212009 for Victoza (liraglutide), 2009.

(56) References Cited

OTHER PUBLICATIONS

Goldberg, Michael et al., "Challenges for the Oral Delivery of Macromolecules" Nature Reviews Drug Discovery, 2003, vol. 2, pp. 289-294.
Granhall, Charlotte et al., "Safety and Pharmacokinetics of Single and Multiple Ascending Doses of the Novel Oral Human GLP-1 Analogue, Oral Semaglutide, in Healthy Subjects and Subjects with Type 2 Diabetes" Clinical Pharmacokinetics, published Dec. 18, 2018.
Hellriegel, Edward T. et al., "Interpatient variability in bioavailability is related to the extent of absorption: Implications for bioavailability and bioequivalence studies" Clinical Pharmacology & Therapeutics, Dec. 1996, vol. 60, No. 6, pp. 601-607.
King, Simon, "ViewPoints: Novo Nordisk R&D chief predicts an oral revolution for biologics" Nov. 14, 2018, Available from: [http://www.firstwordpharma.com/print/1604592?tsid=17].
Lee, Hye J., "Protein Drug Oral Delivery: The Recent Progress" Archives of Pharmacal Research, 2002, vol. 25, No. 5, pp. 572-584.
Madsen, Kjeld et al., "Structure-Activity and Protraction Relationship of Long-Acting Glucagon-like Peptide-1 Derivatives: Importance of Fatty Acid Lenght, Polarity, and Bulkiness" J. Med. Chem., 2007, vol. 50, pp. 6126-6132.
Morishita, Mariko et al., "Is the oral route possible for peptide and protein drug delivery?" Drug Discovery Today, Oct. 2006, vol. 11, No. 19/20, pp. 905-910.
Novo Nordisk Company announcement No. 14/2015, dated Feb. 20, 2015.
Novo Nordisk Company announcement No. 52/2015, dated Aug. 26, 2015.
Novo Nordisk Company announcement No. 17/2018, dated Feb. 22, 2018.
Novo Nordisk Company announcement No. 47/2018, dated May 29, 2018.
Novo Nordisk Company announcement No. 51/2018, dated Jun. 20, 2018.
Novo Nordisk Company announcement No. 53/2018, dated Jun. 28, 2018.
Novo Nordisk Company announcement No. 66/2018, dated Aug. 20, 2018.
Novo Nordisk Company announcement No. 74/2018, dated Sep. 20, 2018.
Novo Nordisk Company announcement No. 81/2018, dated Oct. 26, 2018.
Novo Nordisk Company announcement No. 89/2018, dated Nov. 22, 2018.
Novo Nordisk Company announcement No. 90/2018, dated Nov. 23, 2018.
Owens, D.R. et al., "Alternative routes of insulin delivery" Diabetic Medicine, 2003, vol. 20, pp. 886-898.
Thepharmaletter, "'8-10 years ahead' of field in oral delivery, senior execs say Novo is becoming a GLP-1 company" May 16, 2018, [cited Jan. 24, 2019] Available from: [https://www.thepharmaletter.com/article/8-10-years-ahead-of-field-in-oral-delivery-senior-execs-say-novo-nordisk-is-becoming-a-glp-1-company].
Watson, Estelle et al., "Population Pharmacokinetics of Liraglutide, a Once-Daily Human Glucagon-Like Peptide-1 Analog, in Healthy Volunteers and Subjects With Type 2 Diabetes, and Comparison to Twice-Daily Exenatide" J. Clin Pharmacology, 2010, vol. 50, pp. 886-894.
Anonymous, "Eligen@ Technology. Summary and Value Proposition", Emisphere, Feb. 24, 2017, pp. 1-10, URL: https://www.emisphere.com/wp-content/uploads/2017/02/Eligen-Technology-Presentation_2.15-Update.pdf, XP055520567.
Full European prosecution file of EP 2 827 885 BI. Published Jan. 28, 2015, Available at the EPO Register, https://register.epo.org/application?number=EP13709231&lng=en&tab=doclist, accessed May 31, 2019.
Post-published details of trial NCT01037582. First posted Dec. 23, 2009 https://clinicaltrials.gov/ct2/show/NCT01037582, accessed May 31, 2019.

Published details of trial NCT01037582 First Version Dec. 21, 2009 https://clinicaltrials.gov/ct2/history/NCT01037582?A=1&B=1&C=merged#StudyPageTop, accessed May 31, 2019.
Melanie Davies et al., "Effect of Oral Semaglutide Compared With Placebo and Subcutaneous Semaglutide on Glycemic Control in Patients With Type 2 Diabetes: A Randomized Clinical Trial," JAMA the Journal of the American Medical Association, 2017, vol. 318, No. 15, p. 1460.
Steinert et al., "Oral Administration of Glucagon-Like Peptide 1 or Peptide YY 3-36 Affects Food Intake in Healthy Male Subjects," Am J Clin Nutr, Oct. 2010, vol. 92, No. 4, pp. 810-817.
Full European prosecution file of EP 2 827 885 BI. Available at the EPO Register, https://register.epo.org/application?number=EP13709231&lng=en&tab=doclist, accessed May 31, 2019.
Post-published details of trial NCT01037582 https://clinicaltrials.gov/ct2/show/NCT01037582, accessed May 31, 2019.
Published details of trial NCT01037582 (Dec. 2009) https://clinicaltrials.gov/ct2/history/NGT01037582?A=1&B=1&C=merged#StudyPageTop, accessed May 31, 2019.
Steinert et al., 2010, Am J Clin Nutr, vol. 92, pp. 810-817.
Nauck et al., 2012, Abstracts of the 48th European Association for the Study of Diabetes Annual Meeting of the EASD, Oct. 1-5, 2012, Berlin, Germany, Diabetologia, 2012, vol. 55, Suppl, S7.
Fonseca et al., "Efficacy and Safety of the Once-Daily GLP-1 Receptor Agonist Lixisenatide in Monotherapy," Diabetes Care, 2012, vol. 35, pp. 1225-1231.
Study NCT02014259, version 1, published Dec. 18, 2013, accessed Jun. 5, 2019.
"Drug Absorption, Distribution and Elimination; Pharmacokinetics" http://www.columbia.edu/itc/gsas/g9600/2004/GrazianoReadings/Drugabs.pdf, available since at least Apr. 24, 2006, accessed on Jun. 3, 2019.
"Standards of Medical Care in Diabetes—2010", Diabetes Care, vol. 33, supplement 1, Jan. 2010, pp. S11-S61.
Andrew D. Morris, MD, "Addressing dosing frequency in diabetes: a simple approach to improving adherence to therapy and clinical outcomes," The Diabetes Educator, 2003, vol. 29, No. 3, pp. 440-453.
B.J. Aungst, "Absorption Enhancers: Applications and Advances," The AAPS Journal, 2012, vol. 14, No. 1, pp. 10-18.
ClinicalTrials.gov archive: History of Changes for Study NCT01686945, trackchange of version of Apr. 15, 2013 (published Apr. 16, 2013) as compared to version of Sep. 13, 2012 (published Sep. 18, 2012).
ClinicalTrials.gov archive: History of Changes for Study NCT01923181 (NN9924-3790).
Clinicaltrials.gov, NCT01686945, page as viewed in Apr. 2013, https://clinicaltrials.gov/ct2/history/NCT01686945?A=5&B=5&C=merged#StudyPageTop.
Coskun et al., "LY3298176, a novel dual GIP and GLP-1 receptor agonist for the treatment of type 2 diabetes mellitus: From discovery to clinical proof of concept," Molecular Metabolism, 2018, vol. 18, pp. 3-14.
David J. Edmonds et al., "Oral GLP-1 Modulators for the Treatment of Diabetes". Annual Reports in Medicinal Chemistry, 2013, 1st edition, vol. 48, Chapter 9, pp. 119-130.
DJ. Birkett, "Pharmacokinetics made easy 11 Designing dose regimens," Australian Prescriber, 1996, vol. 19, No. 3, pp. 76-88.
E. Mutschler et al., Mutschler Arzneimittelwirkungen, Lehrbuch der Pharmakologie und Toxikologie, 8th edition 2001, pp. 48-51.
Emisphere Annual Report and Proxy 2013, publicly available at the latest on Apr. 17, 2014.
EU Clinical Trials Register Summary EudraCT No. 2012-004994-16 (NN9924-3790), published Jul. 30, 2013, accessed Jun. 7, 2019.
EU Leaflet of Linagliptin, 1st authorization in EU: Aug. 24, 2011 (p. 2, 3 & 13).
EU Leaflet of Linagliptin-Metformin, 1st authorization in EU: Jul. 20, 2012 (p. 2, 3 & 21).
EU Leaflet of Metformin, 1st authorization in EU: Jul. 31, 2001 (p. 1, 2 & 11).
EU Leaflet of Saxagliptin, 1st authorization in EU: Oct. 1, 2009 (p. 1 & 18).
EU Leaflet of Sitagliptin, 1st authorization in EU: Mar. 21, 2007 (p. 2, 3 & 16).

(56) References Cited

OTHER PUBLICATIONS

EU Leaflet of Sitagliptin-Metformin, 1st authorization in EU: Jul. 16, 2008 (p. 2, 3 & 20).
EU Leaflet of Vildagliptin, 1st authorization in EU: Sep. 26, 2007(p. 2, 3 & 18).
EU Leaflet of Vildagliptin-Metformin, 1st authorization in EU: Nov. 14, 2007 (p. 2, 3 & 21).
European Patent Application 13166205, filed May 2, 2013.
Geiser et al., "Clinical Pharmacokinetics of Dulaglutide in Patients with Type 2 Diabetes: Analyses of Data from Clinical Trials". Clinical Pharmacokinetics, 2016, vol. 55, pp. 625-634.
Granhall et al, Safety and Pharmacokinetics of Single and Multiple Ascending Doses of the Novel Oral Human GLP-1 Analogue, Oral Semaglutide, in Healthy Subjects and Subjects with Type 2 Diabetes, Clinical Pharmacokinetics, Dec. 2018.
Leon Shargel, Applied Biopharmaceutics and Pharmacokinetics, 6th edition, 2012, Chapter 8, Multiple-Dosage Regimens, pp. 153-175.
Linda Felton, Remington, Essentials of Pharmaceutics, 2012, Chapter 37, pp. 708-709 and 712-713.
M. Gonzalez Brao, "48th Annual Meeting of the European Association for the Study of Diabetes (EASD)," Drugs of the Future, 2012, vol. 37, No. 12, pp. 871-878.
Malcolm Rowland et al., "Clinical Pharmacokinetics and Pharmacodynamics : Concepts and Applications," Chapter 11—Multiple-Dose Regimens (pp. 293-329); 4th ed.; Philadelphia: Wolters Kluwer Health/Lippincott William & Wilkins, 2011.
Product details regarding "David J. Edmonds et al., Oral GLP-1 Modulators for the Treatment of Diabetes". Annual Reports in Medicinal Chemistry (2013), 1st edition, vol. 48, chapter 9, pp. 119-130, from amazon.com, accessed on May 3, 2019.
Prosecution file of EP2991671B1, available at the EPO Register, the pdf is not attached. https://register.epo.org/application?number=EP14721834&lng=en&tab=doclist, accessed Jun. 14, 2019.
Quianzon et al., "Lixisenatide—Once daily glucagon-like peptide-1 receptor agonist in the management of type 2 diabetes," 2011, US Endocrinology, Diabetes Management, vol. 7, No. 2, pp. 104-109.
Rosenstock et al., "Potential of albiglutide, a long-acting GLP-1 receptor agonist, in type 2 diabetes: a randomized controlled trial exploring weekly, biweekly, and monthly dosing". Diabetes Care, 2009, vol. 32, No. 10, pp. 1880-1886.
S. Dhillon et al., "Basic Pharmacokinetics," Clinical Pharmacokinetics, 2006, Pharmaceutical Press, London; Chapter 1, pp. 1-44.
Sarfaraz K. Niazi, Handbook of Bioequivalence Testing, 2007, p. 13-15.
Schematic overview of sequences and plasma half-life in humans of "GLP-1 peptides".
Sisson, "Liraglutide: clinical pharmacology and considerations for therapy," Pharmacotherapy, 2011, vol. 31, pp. 896-911.
Study NCT01686945, version 1, published Sep. 18, 2012, accessed Jun. 6, 2019.
Banakar et al, Critical Considerations in Pharmaceutical Bioequivalence Testing, Journal of Pharmacy of University of Marmara, 1995, vol. 11 Nos. 1-2, pp. 55-80.
Emisphere Technologies, Inc., Form 10-K, 2013 Annual Report, Published Mar. 31, 2014.
American Veterinary Medical Association, "The Veterinarian-Client-Patient Relationship (VCPR)," https://www.avma.org/policies/veterinarian-client-patient-relationship, accessed Mar. 11, 2020.
Schematic drawing of tablets E and F described in EP Patent No. 2827885, issued Aug. 15, 2018.
Overview of claim 1 of the main and auxiliary requests, European Application No. EP2651398, filed May 14, 2013.
GenScript, "Peptide YY (PYY) (3-36), human," https://www.genscript.com/peptide/RP10354-Peptide_YY_PYY_3_36_human.html, accessed Jan. 27, 2020.
Study NCT01866748, version 1, published May 31, 2013, accessed Jun. 6, 2019.
Study NCT01923181, version 1, published Aug. 15, 2013, accessed Jun. 5, 2019.
Submission of Novo Nordisk dated Feb. 15, 2019 in response to oppositions against EP2651398B1.
Cahae S Y et al., Journal Title: Journal of the Controlled Release,Title: The Fatty Acid Conjugated Exendin-4 Analogs for Type 2 Antidiabetic Therapeutics ,Year: 2010,vol. 144,pp. 10-16.
EP09179390.1 Priority Application Filed on Dec. 16, 2009 by Novo Nordisk.
EP10190515.6 Priority Application Filed on Nov. 9, 2010 by Novo Nordisk.
Dolensky et al., "New Building Blocks for Fluorinated Imidazole," Jorunal of Organic Chemistry, vol. 66(13), pp. 4687-4691 (2001).
Knudsen et al., "Potent Derivatives of Glucagon-Like Peptide-1 With Pharmacokinetic Properties Suitable for Once Daily Administration," Journal of Medicinal Chemistry, 2000, vol. 43(9), pp. 1664-1669.
Dumelin et al.., "A Portable Albumin Binder From a DNA-Encoded Chemical Library", Angewandte Chemie (International Edition in English), vol. 47(17), pp. 3196-3201 (2008).
Rawley SS et al. Journal of Organic Chemistry. "Oxidation of Primary, Secondary, and Tertiary Amines With Neutral Permanganate. A Simple Method for Degrading Amines to Aldehydes and Ketones." 1967. vol. 32(10). pp. 3129-3131.
Travis B R et al. Organic Letters. "Facile Oxidation of Aldehydes to Acids and Esters With Oxone." 2003. vol. 5(7). pp. 1031-1034.
Murage E N et al. Bioorganic & Medicinal Chemistry. "Search for ¿-Helical Propensity in the Receptor-Bound Conformation of Glucagon-Like Peptide-1." 2008. vol. 16. pp. 10106-10112.
Ruan Guo-Hu et al "Progress of Pharmaceutical Studies on Diabetes" Practical Pharmacy and Clinic, 2007, vol. 10, No. 1, pp. 56-57.
"Formulation and Analytical Development for Low-Dose Oral Drug Products," Wiley, 2009, p. 194.
"International Nonproprietary Names for Pharmaceutical Substances (INN)," WHO Drug Information, 2009, vol. 23, No. 2, p. 129.
"Sodium Lauryl Sulfate," Handbook of Pharmaceutical Excipients, 2009, 6th Edition, pp. 651-653.
Ajaz S. Hussain, "A Collaborative Search for Efficient Methods of Ensuring Unchanged Product Quality and Performance During Scale-Up of Immediate-Release Solid Oral Dosage Forms," Pharmaceutical Process Scale-Up, 2002, 1st Edition, Chapter 11, pp. 325-352.
Bai et al., Excipient Development for Pharmaceutical, Biotechnology, and Drug Delivery Systems, 2006, Chapter 12, pp. 181-185.
C. M. Keck et al., "Moderne Pharmazeutische Technologie—Lehbuch fur Studierende," 1. Auflage (2009), Kapitel 1.2 H. J. Ji.inginger, "Delivery Systeme fur die perorale Applikation van Peptiden," pp. 1-14.
European Application No. 12172739.0, filed Jun. 20, 2012.
File History of European Patent 2827845, filed Mar. 15, 2013.
File History of U.S. Appl. No. 61/662,456, filed Jun. 21, 2012.
Handbook of Pharmaceutical Excipients, 6th Edition, 2009, pp. 404-407 and 651-653.
History of changes for clinical trial NCT01037582, from Mar. 17, 2011, https://clinicaltrials.gov/ct2/history/NCT01037582?A=5&C=merged#StudyPageTop.
Kikuta et al., "Effect of Mixing Time on the Lubricating Properties of Magnesium Stearate and the Final Characteristics of the Compressed Tablets," Drug Development and Industrial Pharmacy, 1994, vol. 20, No. 3, pp. 343-355.
Kusher IV et al., "Scale-up model describing the impact of lubrication on tablet tensile strength," International Journal of Pharmaceutics, vol. 399, Nos. 1-2, pp. 19-30.
Lieberman et al., Pharmaceutical Dosage Forms: Tablets, 2nd Edition, 1989, Chapter 5, pp. 247-284.
Parikh, Handbook of Pharmaceutical Granulation Technology, 3rd Edition, 2010, Informa Healthcare, pp. 2-3.
Remington, The Science and Practice of Pharmacy, 21st Edition, 2005, Lippincott, Williams & Wilkins, pp. 677, 892-893, 896, and 1040.
Sakr et al., "Oral Solid Dosage Forms," Remington, Essentials of Pharmaceutics, 1st Edition, Chapter 30, pp. 581-610.
Summary of Product Characteristics for Valtrex 500mg Tablets, 2019.

(56) References Cited

OTHER PUBLICATIONS

Teng et al., "Systematical approach of formulation and process development using roller compaction," European Journal of Pharmaceutics and Biopharmaceutics, 2009, vol. 73, pp. 219-229.
The Handbook of Pharmaceutical Granulation Technology, Chapters 2, 8, and 9, 2010.
Uros Markoja, Semaglutide-Experiment report for opposition against EP2827845B1, dated Sep. 24, 2019, pp. 1-6.
Valtrex prescribing information, Oct. 2007.
Venables et al., "Powder Mixing," Drug Development and Industrial Pharmacy, 2001, vol. 27, No. 7, pp. 599-612.
Tyagi et al., "Oral peptide delivery: Translational challenges due to physiological effects," J. Controlled Release, 2018, vol. 287, pp. 167-176.
Dahlgren et al., "Intestinal absorption-modifying excipients: A current update on preclinical in vivo evaluations," European J. of Pharm. and Biopharmaceutics, 2019, vol. 142, pp. 411-420.
Figures presenting plasma concentration, described in EU Patent No. 2991671, issued Aug. 15, 2018.
FDA News Release, "FDA approved first oral GLP-1 treatment for type 2 diabetes," Sep. 20, 2019.
Carly Helfand, "Novo Nordisk wins FDA green light for "holy grail" diabetes drug Rybelsus," Fierce Pharma, Sep. 20, 2019, https://www.fiercepharma.com/pharma/novo-nordisk-wins-fda-green-light-for-holy-grail-oral-semaglutide, accessed Oct. 4, 2019.
Runge et al., "Crystal Structure of the Ligand-Bound Glucagon-Like Peptide-1 Receptor Extracellular Domain," J Biol Chem 2008, vol. 283, No. 17, pp. 11340-11347.
Adelhorst, K et al Journal of Biological Chemistry Structure Activity Studies of GLP-1 1994 269 9 6275-6278.
Knudsen, L.B. Journal of Medicinal Chemistry Glucagon-Like Peptide-1: The Basis of a New Class of Treatment for Type 2 Diabetes 2004 47 17 4128-4134.
Leger et al., "Identification of CJC-1131-Albumin Bioconjugate as a Stable and Bioactive GLP-1 (7-36) Analog," Bioorganic and Medicinal Chemistry Letters, vol. 14, pp. 4395-4398 (2004).
Pan, 2006 Journal of Biological Chemistry vol. 281 pp. 12506-12515.
The Medical Dictionary Online. http://cancerweb.ncl.ac.uklomd/about.html. 2005.
Nauck, M A. Regulatory Peptides. "Glucagon-Like Peptide 1 and its Derivatives in the Treatment od Diabetes." 2005. vol. 128(2). pp. 135-148.
David M. Irwin, Trout and chicken Proglucagon: Alternative Splicing Generates mRNA Transcripts Encoding Glucagon-Like Peptide 2, Molecular Endocrinology, 1995, vol. 9 No. 3, 267-277.
Table summarizing the components of the tablet compositions B to F, described in EP Patent No. 2827885, issued Aug. 15, 2018.
National Institute of Diabetes and Digestive and Kidney Diseases,"Prescription Medications to Treat Overweight and Obesity," Jul. 2016, 10 pages, retrieved on Apr. 13, 2020., URL: https://www.niddk.nih.gov/health-information/weight-management/prescription-medications-treat-overweight-obesity.
Physicians' Desk Reference, 54th Edition, 2000, p. 1291.
Physicians' Desk Reference, 63rd Edition, 2009, p. 1638.
W.K. Sietsema, "The absolute oral bioavailability of selected drugs." Mar. 1989, International Journal of Clinical Pharmacology, Therapy and Toxicology, vol. 27, No. 4, pp. 179-211.
Declaration of Doctor Peter Rue, for EP2827885 dated Jul. 29, 2020.
Declaration of Professor Leon Aarons for EP2827885 dated Jul. 29 2020.
Shajahan et al., A flexible technology for modified-release drugs: Multiple-unit pellet system (MUPS) May 2009, Journal of Controlled Release, vol. 147, No. 1, pp. 2-16.
Arbit et al. "Oral heparin: status review". Thrombosis J, May 2006, vol. 4, No. 6, pp. 1-7.
Emisphere Announces License Agreement With Novo Nordisk to Develop Oral Formulation of GLP-1 Receptor Agonists for Diabetes, Jun. 23, 2008 retrieved from https://www.biospace.com/article/releases/emisphere-technologies-inc-announces-license-agreement-with-novo-nordisk-inc-to-develop-oral-formulation-of-glp-1-receptor-agonists-for-diabetes-/, 5 pages, retrieved on Dec. 16, 2020.
European Medicines Agency, Rybelsus EPAR Public Assessment Report, Jan. 30, 2020, pp. 1-152, p. 72.
Notice of Opposition by Galenicum, filed Dec. 9, 2020 in European Patent 3326620.
Notice of Opposition by Hexel Ag, filed Dec. 8, 2020 in European Patent 3326620.
Novo Nordisk starts phase 1 trial with long-acting oral GLP-1 analogue, Jan. 13, 2010, 2 pages retrieved from https://pipelinereview.com/index.php/2010011332046/Small-Molecules/Novo-Nordisk-starts-phase-1-trial-with-long-acting-oral-GLP-1-analogue.html, retrieved on Dec. 16, 2020.
Novo Nordisk, "Novo Nordisk to acquire Emisphere Technologies and obtain ownership of the Eligen® SNAC oral delivery technology", Nov. 6, 2020 retrieved from <https://www.novonordisk.com/content/nncorp/global/en/news-and-media/news-and-ir-materials/news-details.html?id=33374>, 3 pages retrieved on Dec. 16, 2020.
Notice of Opposition by Teva filed Dec. 4, 2020 in European Patent 3326620.

* cited by examiner

SEQUENCE LISTING

```
<160> NUMBER OF SEQ ID NOS: 2

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 40
<212> TYPE: PRT
<213> ORGANISM: Heloderma suspectum

<400> SEQUENCE: 2

His Gly Glu Gly Thr Phe Ile Thr Ser Asp Leu Ser Lys Gln Met Glu
1               5                   10                  15

Glu Glu Ala Val Arg Leu Phe Ile Glu Trp Leu Lys Asn Gly Gly Pro
            20                  25                  30

Ser Ser Gly Ala Pro Pro Pro Ser
            35                  40
```

TABLET FORMULATION COMPRISING A GLP-1 PEPTIDE AND A DELIVERY AGENT

CROSS-REFERENCE TO RELATED APPLICATIONS

This application is a continuation of U.S. application Ser. No. 14/409,021, filed Dec. 18, 2014, which is a 35 U.S.C. § 371 National Stage application of International Application PCT/EP2013/062751 (WO 2013/189988), filed Jun. 19, 2013, which claimed priority of European Patent Application 12172739.0, filed Jun. 20, 2012; this application claims priority under 35 U.S.C. § 119 of U.S. Provisional Application 61/662,456; filed Jun. 21, 2012; the contents of all above-named applications are incorporated herein by reference.

The present invention relates to solid compositions comprising a pharmaceutically active peptide and a delivery agent, which is a salt of N-(8-(2-hydroxybenzoyl)amino) caprylate (NAC), as well as processes for their preparation and uses thereof.

SEQUENCE LISTING

The instant application contains a Sequence Listing which has been submitted in ASCII format via EFS-Web and is hereby incorporated by reference in its entirety. Said ASCII copy, created on Mar. 6, 2018, is named 8530US02_SeqList.txt and is 2 kilobytes in size.

BACKGROUND

One of the main challenges in oral delivery of proteins and peptides is the inability of these compounds to be readily transported across the membranes of the gastrointestinal tract. The delivery agent SNAC has previously been shown to improve the bioavailability of orally administered peptides.

WO 2012/080471 A1, WO 2008/109385 A2 and WO 2010/020978 A1 are related to oral compositions comprising a peptide drug and a delivery agent. However improved oral compositions are still needed.

The present invention relates to further improvements of the bioavailability by oral administration of compositions of such peptides, in particular of GLP-1 peptides.

SUMMARY

In some embodiments the invention relates to a tablet comprising a granulate comprising i) no more than 15% (w/w) GLP-1 peptide, and ii) at least 50% (w/w) salt of NAC, wherein said tablet has a) a bulk density of at least 0.90 g/cm$^3$, b) a median pore diameter of no more than 1.5 µm, c) a maximum pore diameter of no more than 4 µm, and/or d) a crushing strength of at least 50 N, wherein said bulk density is determined by Assay (Ia) as described herein, wherein said median pore diameter or maximum pore diameter is determined by Assay (IIb) as described herein, wherein said crushing strength is determined by Assay (III) as described herein, and wherein said disintegration time is determined by Assay (IV) as described herein.

In some embodiments the invention relates to a tablet comprising a granulate comprising i) no more than 15% (w/w) peptide, and ii) at least 55% (w/w) salt of NAC, wherein said tablet has a) a bulk density of at least 0.90 g/cm$^3$, b) a median pore diameter of no more than 1.5 µm, c) a maximum pore diameter of no more than 4 µm, and/or d) a crushing strength of at least 50 N, wherein said bulk density is determined by Assay (Ia) as described herein, wherein said median pore diameter or maximum pore diameter is determined by Assay (IIb) as described herein, wherein said crushing strength is determined by Assay (III) as described herein, and wherein said disintegration time is determined by Assay (IV) as described herein.

In some embodiments the invention relates to a tablet as defined herein for use in medicine, such as for treating type 2 diabetes or obesity.

In some embodiments the invention relates to a granulate as defined herein. In some embodiments the invention relates to a process for the preparation of a tablet comprising a granulate comprising i) no more than 15% (w/w) peptide, such as GLP-1 peptide, and ii) at least 50% (w/w) salt of NAC, said method comprising the step of exerting a compression force when punching said tablet of at least 5 kN, such as at least 10 kN or at least 15 kN, or at least 4 kN/cm$^2$, such as at least 6 kN/cm$^2$ or at least 8 kN/cm$^2$, wherein said process optionally comprises a pre-compression step, and wherein said tablet optionally is as defined herein.

In some embodiments the invention relates to a method for controlling porosity of a group of tablets, said method comprising the steps of: a) determining the near-infrared (NIR) spectrum of one or more of said tablets; b) comparing said spectrum to a reference NIR spectrum, or performing a statistical analysis of said spectrum to determine the tablet porosity; c) optionally adjusting the tabletting parameters during tabletting in order to improve the NIR spectrum or porosity of the tablets; and d) selecting a subgroup of tablets with a NIR spectrum or porosity within a predetermined range; wherein said method optionally is an at-line or an in-line NIR method, and wherein said tablet optionally is as defined herein.

DESCRIPTION

Figure 1:
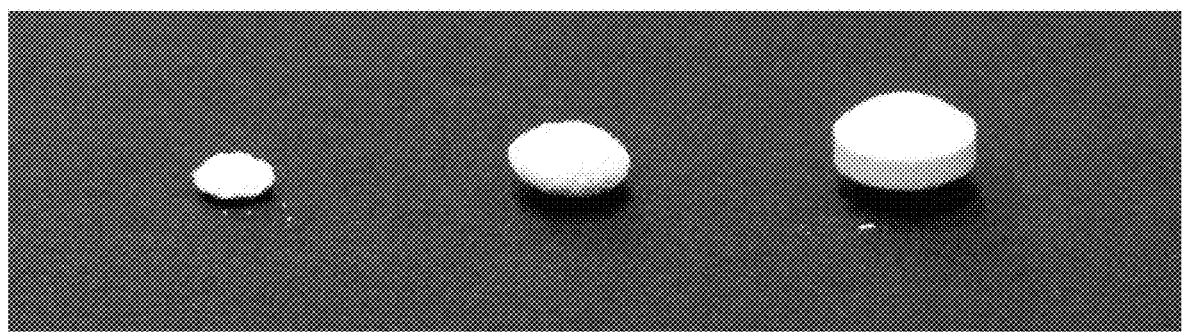
FIG. 1 shows surface erosion of Tablet A before (right), after 5 minutes (middle) and after 10 minutes (left) disintegration test.

The present invention relates to improved tablets comprising a peptide, such as a GLP-1 peptide, and a delivery agent, which is a salt of NAC. The present inventors surprisingly found that the requirements to physical parameters of tablets, such as density, porosity and/or crushing strength, as well as the methods of preparation of tablets according to the present invention provide tablets with improved bioavailability of peptides, such as acylated peptides.

Generally, the term "bioavailability" as used herein refers to the fraction of an administered dose of an active pharmaceutical ingredient (API) and/or active moieties, such as a peptide or a GLP-1 peptide as defined herein, which reaches the systemic circulation. By definition, when an API and/or active moieties are administered intravenously, its bioavailability is 100%. However, when it is administered via other routes (such as orally), its bioavailability decreases (due to incomplete absorption). Knowledge about bioavailability is important when calculating dosages for non-intravenous routes of administration.

Absolute oral bioavailability is calculated as the relative exposure of the API and/or active moieties in systemic circulation following oral administration (estimated as the area under the plasma concentration versus time curve) compared to the exposure of the API and/or active moieties following intravenous administration.

Compositions

The present invention relates to a composition in the form of a tablet. In some embodiments the composition of the invention is for oral administration.

In some embodiments the tablet comprises a granulate comprising i) no more than 15% (w/w) peptide, and ii) at least 50% (w/w) salt of NAC, wherein said tablet has a) a bulk density of at least 0.90 g/cm$^3$; b) a median pore diameter of no more than 1.5 μm; and/or c) a maximum pore diameter of no more than 4 μm. In some embodiments the invention relates to a tablet comprising a granulate comprising i) no more than 15% (w/w) peptide, and ii) at least 50% (w/w) salt of NAC, wherein said tablet has a) a bulk density of at least 0.90 g/cm$^3$; b) a median pore diameter of no more than 1.5 μm; c) a maximum pore diameter of no more than 4 μm; and/or d) a crushing strength of at least 50 N.

In some embodiments the invention relates to a tablet comprising a granulate comprising i) no more than 15% (w/w) peptide, and ii) at least 50% (w/w) salt of NAC, wherein said tablet has a) a bulk density, such as a bulk density, of at least 0.90 g/cm$^3$; b) a median pore diameter of no more than 1.5 μm; c) a maximum pore diameter of no more than 4 μm; d) a crushing strength of at least 50 N; and/or e) a disintegration time of 12-18 minutes for a tablet with a total weight of 300-500 mg comprising at least 60% (w/w) salt of NAC.

In some embodiments, at tablet of the invention is surface eroding. By the term "surface eroding" is herein meant that the material detachment from the tablet is from the surface of the tablet as e.g. depicted in FIG. 1. A surface eroding tablet is thus the opposite of a disintegrating type of a tablet, where the tablet material is disintegrated into primary particles or granules and hereby accelerating the dissolution process.

In some embodiments the term "granulate" refers to one or more granules. In some embodiments the term "granule" refers to particles gathered into larger particles.

In some embodiments the tablet comprises a granulate comprising a peptide, a salt of NAC and optionally a binder. In some embodiments the composition comprises an intragranular and an extragranular part, wherein said extragranular part comprises at least part of a lubricant and optionally a filler.

In some embodiments the tablet comprises less than 15% (w/w) peptide, at least 50% (w/w) salt of NAC, less than 10% (w/w) binder, 5-40% (w/w) filler, and less than 10% (w/w) lubricant. In some embodiments the tablet comprises a) a granulate comprising i) 1-15% (w/w) peptide, ii) 55-85% (w/w) salt of NAC, and iii) 1-20% (w/w) binder; b) 10-35% (w/w) filler; and c) 0.5-3% (w/w) lubricant. In some embodiments the tablet comprises a) a granulate comprising i) 1-100 mg, such as 10 mg, peptide, ii) 100-1000 mg, such as 300 mg, salt of NAC, and iii) 1-20 mg, such as 8 mg, binder; b) 20-200 mg, such as 100 mg, filler; and c) 0.5-8 mg, such as 2-8 mg, lubricant.

In some embodiments the invention relates to a granulate as defined herein. In some embodiments the granulate comprises i) no more than 15% (w/w) peptide, and ii) at least 50% (w/w) salt of NAC. In some embodiments the granulate comprises i) 1-15% (w/w) peptide, ii) 55-85% (w/w) salt of NAC, and iii) 1-20% (w/w) binder. In some embodiments the granulate comprises i) 1-100 mg, such as 10 mg, peptide, ii) 100-1000 mg, such as 300 mg, salt of NAC, and iii) 1-20 mg, such as 8 mg, povidone. In some embodiments the granulate comprises at least 80% (w/w) delivery agent, less than 10% (w/w) lubricant, and optionally less than 20% filler. In some embodiments the granulate comprises a peptide, at least 10% (w/w) filler and less than 40% (w/w) binder.

In some embodiments the composition or granulate comprises at least one pharmaceutically acceptable excipient. The term "excipient" as used herein broadly refers to any component other than the active therapeutic ingredient(s). The excipient may be an inert substance, which is inert in the sense that it substantially does not have any therapeutic and/or prophylactic effect per se. The excipient may serve various purposes, e.g. as a delivery agent, absorption enhancer, vehicle, filler (also known as diluents), binder, lubricant, glidant, disintegrant, crystallization retarders, acidifying agent, alkalizing agent, preservative, antioxidant, buffering agent, chelating agent, complexing agents, surfactant agent, emulsifying and/or solubilizing agents, sweetening agents, wetting agents stabilizing agent, colouring agent, flavouring agent, and/or to improve administration, and/or absorption of the active substance. A person skilled in the art may select one or more of the aforementioned excipients with respect to the particular desired properties of the solid oral dosage form by routine experimentation and without any undue burden. The amount of each excipient used may vary within ranges conventional in the art. Techniques and excipients which may be used to formulate oral dosage forms are described in Handbook of Pharmaceutical Excipients, 6th edition, Rowe et al., Eds., American Pharmaceuticals Association and the Pharmaceutical Press, publications department of the Royal Pharmaceutical Society of Great Britain (2009); and Remington: the Science and Practice of Pharmacy, 21th edition, Gennaro, Ed., Lippincott Williams & Wilkins (2005).

In some embodiments the composition or granulate comprises a filler, such as lactose (e.g. spray-dried lactose, α-lactose, β-lactose, Tabletose®, various grades of Pharmatose®, Microtose® or Fast-FloC®), microcrystalline cellulose (various grades of Avicel®, Elcema®, Vivacel®, Ming Tai® or Solka-Floc®), other cellulose derivatives, sucrose, sorbitol, mannitol, dextrins, dextrans, maltodextrins, dextrose, fructose, kaolin, mannitol, sorbitol, sucrose, sugar, starches or modified starches (including potato starch, maize starch and rice starch), calcium phosphate (e.g. basic calcium phosphate, calcium hydrogen phosphate, dicalcium phosphate hydrate), calcium sulphate, calcium carbonate, or sodium alginate. In some embodiments the filler is microcrystalline cellulose, such as Avicel PH 101, Avicel PH 102, or Avicel PH 200. In some embodiments the composition comprises 5-40% (w/w), such as 10-30% (w/w) or 5-25%

(w/w), filler. In some embodiments said filler is in the intragranular and/or extragranular part of the composition.

In some embodiments the composition or granulate comprises a binder, such as lactose (e.g. spray-dried lactose, α-lactose, β-lactose, Tabletose®, various grades of Pharmatose®, Microtose® or Fast-FloC®), microcrystalline cellulose (various grades of Avicel®, Elcema®, Vivacel®, Ming Tai® or Solka-Floc®), hydroxypropylcellulose, L-hydroxypropylcellulose (low-substituted), hypromellose (HPMC) (e.g. Methocel E, F and K, Metolose SH of Shin-Etsu, Ltd, such as, e.g., the 4,000 cps grades of Methocel E and Metolose 60 SH, the 4,000 cps grades of Methocel F and Metolose 65 SH, the 4,000, 15,000 and 100,000 cps grades of Methocel K; and the 4,000, 15,000, 39,000 and 100,000 grades of Metolose 90 SH), methylcellulose polymers (such as, e.g., Methocel A, Methocel A4C, Methocel A15C, Methocel A4M), hydroxyethylcellulose, ethylcellulose, sodium carboxymethylcellulose, other cellulose derivatives, sucrose, dextrins, maltodextrins, starches or modified starches (including potato starch, maize starch and rice starch), calcium lactate, calcium carbonate, acacia, sodium alginate, agar, carrageenan, gelatin, guar gum, pectin, PEG, or povidone. In some embodiments the binder is povidone, such as povidone K 90. In some embodiments the amount of binder is 0.1-10% (w/w), such as 0.2-4% (w/w) or 0.5-3% (w/w), or such as 1.0-2.5% (w/w). In some embodiments the binder is in the intragranular and/or extragranular part of the composition.

In some embodiments the tablet or granulate does not contain a superdisintegrant, i.e. an ingredient improving disintegrant efficiency such as e.g. sodium starch glycolate, sodium carboxymethyl starch, crospovidone and croscarmellose sodium. In some embodiments the composition or granulate comprises a disintegrant, such as alginic acid, alginates, microcrystalline cellulose, hydroxypropyl cellulose, other cellulose derivatives, polacrillin potassium, starch, or pregelatinized starch.

In some embodiments the composition or granulate comprises a lubricant, such as stearic acid, magnesium stearate, calcium stearate or other metallic stearate, talc, waxes, glycerides, light mineral oil, glyceryl behenate, hydrogenated vegetable oils, sodium stearyl fumarate, polyethylene glycols, alkyl sulfates, or sodium benzoate. In some embodiments the composition or granulate comprises a lubricant, such as magnesium silicate, talc, or colloidal silica. In some embodiments the lubricant is magnesium stearate. In some embodiments the amount of lubricant is 0.1-10% (w/w) or 0.5-5% (w/w), such as 1-3.5% (w/w), 0.5-3% (w/w) or 1.0-2.5% (w/w). In some embodiments the lubricant is in the intragranular and/or extragranular part of the composition.

Still further, the composition or granulate of the invention may be formulated as is known in the art of oral formulations of insulinotropic compounds.

In some embodiments the weight of the tablet is in the range of 150 mg to 1000 mg, such as in the range of 300-600 mg or such as 300-500 mg.

Methods of Preparation of Pharmaceutical Compositions

In some embodiments the invention relates to a process for the preparation of a tablet comprising a granulate comprising i) no more than 15% (w/w) peptide, such as GLP-1 peptide, and ii) at least 50% (w/w) salt of NAC, said method comprising the step of exerting a compression force when punching said tablet of at least 5 kN, such as 5-25 kN, and/or at least 4 kN/cm$^2$. In some embodiments the compression force is in the range of 5-25 kN. In some embodiments the compression force is at least 5 kN, such as at least 10 kN or at least 15 kN. In some embodiments the compression force is no more than 25 kN, such as no more than 20 kN. In some embodiments the compression force is at least 4 kN/cm$^2$, such as at least 6 kN/cm$^2$ or at least 8 kN/cm$^2$. In some embodiments the process comprises a pre-compression step. In some embodiments the tablet or granulate is as defined herein.

The composition of the invention may be prepared as is known in the art. In some embodiments the composition or the granulate may be prepared as described in the examples herein. The composition may comprise one or more intragranular parts and an extragranular part, wherein the intragranular parts have been granulated, and wherein the extragranular part has been added after granulation. The extragranular part may comprise a lubricant.

In some embodiments two or more ingredients of the composition are blended. To prepare a dry blend of tabletting material, the various components are weighed, optionally delumped and then combined. The mixing of the components may be carried out until a homogeneous blend is obtained.

In some embodiments at least a part of the composition is dry granulated or wet granulated. A granulate may be produced in a manner known to a person skilled in the art, for example by dry granulation techniques in which the pharmaceutically active agent and/or delivery agents are compacted with the excipients to form relatively large moldings, for example slugs or ribbons, which are comminuted by grinding, and the ground material serves as the tabletting material to be later compressed into tablets. Suitable equipment for dry granulation includes but is not limited to roller compaction equipment from Gerteis, such as Gerteis MINI-PACTOR. In some embodiments the granulate is prepared by roller compaction. In some embodiments the moldings from the roller compactions process are comminuted into granules. Alternatively, a granulate can be obtained by wet granulation which may be carried out by mixing the pharmaceutically active agent dissolved in water with a dry blend of the delivery agents and optionally one or more excipients followed by drying of the granulate.

To compress the tabletting material into a solid oral dosage form, for example a tablet, a tablet press may be used. In a tabletting press, the tabletting material is filled (e.g. force fed or gravity fed) into a die cavity. The tabletting material is then compressed by a punch with pressure. Subsequently, the resulting compact, or tablet is ejected from the tabletting press. The above mentioned compression process is subsequently referred to herein as the "compression process". Suitable tablet presses include, but are not limited to, rotary tablet presses and eccentric tablet presses. Examples of tablet presses include, but are not limited to, the Fette 102i (Fette GmbH), the Korsch XL100, the Korsch PH 106 rotary tablet press (Korsch AG, Germany), the Korsch EK-O eccentric tabletting press (KorschA G, Germany), the DIAF TM20 press (Denmark) and the Manesty F-Press (Manesty Machines Ltd., United Kingdom). By the term "exerting a compression force" is thus meant compressing the tabletting material with a specified force as e.g. measured in Newton such as e.g. at least 5 kN or at least 4 kN/cm$^2$.

As used herein "pre-compression" is intended to mean the application of a preliminary compression force just before a second main compression force is applied. During the pre-compression step the height of the powder compact is reduced to no more than 2 times the height of the final tablet, such as no more than 2 times or no more than 1.3 times the final height of the tablet.

In some embodiments the invention relates to a pharmaceutical composition obtained by the process as defined herein.

In some embodiments the tablet is prepared by exerting a compression force in the range of 5-25 kN. In some embodiments the tablet is prepared by exerting a compression force of at least 5 kN, such as at least 10 kN or at least 15 kN. In some embodiments the tablet is prepared by exerting a compression force of no more than 25 kN, such as no more than 20 kN. In some embodiments the term "resistance to crushing of tablets" or "crushing strength" has the meaning defined in section 2.9.8 in the European Pharmacopoeia 7.5, 7th edition 2012; crushing strength may be measured inter alia in Newton (N) or kilopond (kP) using a jaw speed of 20 N/s (1 kP equals 9.807 N).

In some embodiments the term "roller compaction force" means the force between the rolls of the roller compactor when compacting materials into a continuous strip of compressed material as determined by a pressure transducer that converts the hydraulic pressure into electrical signal; the roller compaction force may be measured in kiloNewton (kN) or in kiloNewton per roll width (kN/cm).

Physical Properties and In Vitro Methods

Density is the ratio of mass to volume. Powder compression is defined as the reduction of a powder volume due to the application of a mechanical force. Bonds are formed between granules during compression because of the increased proximity of particle surface accomplished during compression, which provide coherence and mechanical resistance to the powder compact. During compression repacking and deformation of granules (elastic or plastic deformation) will occur. Bulk density is the mass of the tablet divided by total volume of the tablet defined by the outer boundary of the tablet. This volume is determined by the dimension of the punches (cup volume), die hole surface area and tablet band thickness used for compression into a tablet. The bulk density can be calculated as (tablet mass/(2×(cup volume)+(die hole surface area)×((tablet thickness)−2×(cup depth)))). Alternatively, the bulk density can be determined by submerging the tablet into a non-wetting liquid at atmospheric pressure, like mercury, and determining the displaced volume. In some embodiments the tablet of the invention has a bulk density of at least 0.90 g/cm³, such as at least 0.95 g/cm³ or at least 1.0 g/cm³, or such as at least 1.1 g/cm³ or at least 1.2 g/cm³. In some embodiments the bulk density is 1.10-1.19 g/cm³, such as 1.13-1.18 g/cm³, such as about 1.14, about 1.15, about 1.16, or about 1.17 g/cm³. In some embodiments the bulk density is no more than 1.19 g/cm³. Bulk density of compositions of the invention may be determined as described in Assay (I) or (IIb) herein.

The microstructure of pharmaceutical solid dosage forms (porosity, pore volume-size distribution, specific surface area) can be investigated by different methods, e.g. mercury porosimetry. Porosity is a measure of the void spaces in a tablet, and is a fraction of the volume of voids (i.e. volume of pores) over the total volume, between 0-1, or as a percentage between 0-100%. Porosity can be calculated as (1—(tablet bulk density/granule density)) or (1—(tablet bulk density/tablet skeletal density)). Alternatively, the pore volume can be determined by mercury intrusion into the tablet. Since mercury does not wet most substances and will not spontaneously penetrate pores by capillary action, it must be forced into the pores by the application of external pressure. In practice, the tablet is evacuated, and then immersed in mercury. At laboratory pressures mercury will not enter the pores of the tablet. The pressure on the mercury is then raised in a stepwise fashion, forcing the mercury into the pores of the tablet. When the pressure is sufficiently high, the mercury will invade all the pores. A measurement of the volume of mercury intruded into the tablets provides the pore volume directly. The pore diameter is the average or effective diameter of the openings in the tablet. There is a direct relation between pore size and amount of mercury intrusion at a given pressure. At any pressure, the pores into which mercury has intruded have diameters greater than $$D = -4\gamma \cos\theta / P \quad (1)$$

wherein D is the diameter, γ is surface tension of mercury and θ is the contact angle between the sample and mercury, P is pressure. By measuring the volume of mercury that intrudes into the sample material with each pressure change, the volume of pores in the corresponding size class is known. The contact angle of mercury with most solids is between 135° and 142°, so an average of 140° can be taken without much error. The surface tension of mercury at 20° C. under vacuum is 480 mN/m. Then equation 1 can be reduced to:

$$D = (1470 \text{ kPa} \times \mu m)/P \quad (2)$$

Total intrusion volume (ml mercury per gram of tablet) is the total volume on mercury intruded into the sample at the highest applied pressure and is a measure of pore volume from which porosity can be calculated. The median pore diameter can be determined from the cumulative mercury intrusion volume as the pore diameter where 50% of the total volume has been added. The maximum pore diameter can be determined from the cumulative mercury intrusion volume as the pore diameter where mercury starts to intrude into the sample. In some embodiments the tablet has a median pore diameter of no more than 1.5 μm, such as no more than 1.3 μm or no more than 1.0 μm. In some embodiments the tablet has a maximum pore diameter of no more than 4 μm, such as no more than 3.5 μm or no more than 3 μm. Porosity of compositions, including median pore diameter and maximum pore diameter, of the invention may be determined as described in Assay (IIa) or (IIb) herein.

Crushing strength of a tablet is the compressive stress (diametrally applied) required to cause the tablet to fail by fracture. In some embodiments the tablet has a crushing strength of 50-400 N, such as 50-300 N. In some embodiments the tablet has a crushing strength of at least 50 N, such as at least 75 N or at least 100 N. In some embodiments the tablet has a crushing strength of no more than 300 N, such as no more than 250 N. Crushing strength of compositions of the invention may be determined as described in Assay (III) herein.

Disintegration time of compositions of the invention may be determined as described in Assay (IV) herein. In some embodiments the tablet has a disintegration time of 11-18 minutes, such as 12-18 minutes, 12-17 minutes or 13-15 minutes. In some embodiments the tablet has a disintegration time of 11-18 minutes, such as 12-18 minutes, 12-17 minutes or 13-15 minutes, and wherein said tablet has a total weight of 300-500 mg, such as 250-750 mg, and comprises at least 60% (w/w) salt of NAC. In some embodiments the disintegration time is no more than 22 minutes and/or the bulk density is no more than 1.19 g/cm³. In some embodiments the disintegration time is no more than 21 minutes, such as no more than 20 minutes. In some embodiments the tablet of the invention the active ingredient(s) and the delivery agent are released by surface erosion; hence, the tablets becomes smaller and smaller with time by dissolution primarily from the surface from non-disintegrated tablets.

Surface erosion can be shown by visual inspection during the disintegration test; the tablets are surface eroding if the tablet does not break into smaller parts during the first 8 minutes of the disintegration test.

Dissolution of compositions of the invention may be determined as described in Assay (V) herein. In some embodiments the peptide and the salt of NAC are co-released from the tablet as determined by Assay (V) as described herein. In some embodiment co-release of two or more ingredients is defined as dissolved relative amounts of said ingredients within +/−50%, such as +/−25% or +/−10%, of the ingredient having the highest dissolved relative amount compared to the ingredient having the lowest dissolved relative amount at any point in time during the dissolution test according to Assay (V) as described herein; wherein the dissolved relative amount is the amount of an ingredient in solution relative to the total amount of said ingredient.

Oral bioavailability and absorption kinetics of the composition of the invention may be determined according to Assay (VI) as described herein.

Cmax is herein used in connection with salt of NAC for the maximum concentration of salt of NAC in blood plasma after administration and prior to the administration of a second dose, i,e. the peak plasma concentration of salt of NAC after administration.

Peptides

In some embodiments the composition of the invention comprises a peptide. In some embodiments the peptide comprises a lipophilic side chain, such as a peptide comprising an alkyl moiety with at least 14 carbon atoms. In some embodiments the peptide is an acylated peptide. In some embodiments the peptide comprises substituent comprising a fatty acid or a fatty diacid, such as formula (X)

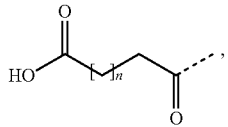

(X)

wherein n is at least 13. In some embodiments the peptide comprises one or more 8-amino-3,6-dioxaoctanoic acid (OEG).

The systemic appearance in plasma of peptides comprising a lipophilic side chain following oral administration is often significantly prolonged relative to the same peptides without lipophilic side chain. In some embodiments a peptide comprising a lipophilic side chain has a protracted mode of action. In some embodiments it is particularly advantageous when a peptide comprising a lipophilic side chain is comprised in a tablet of the invention. It has surprisingly been found by the inventors that a tablet of the invention is particularly suitable when the active component is a peptide comprising a lipophilic side chain. The inventors thus surprisingly found that gradual release of a salt of NAC from the tablet by surface erosion extend the absorption profile of a peptide comprising a lipophilic side chain. In some embodiment tablets of the invention cause a gradual release of salt of NAC leading to a low Cmax in plasma of said salt of NAC in subjects, such as a Cmax of less than 900 ng/ml upon oral administration of a tablet comprising approximately 1 mmol salt of NAC.

In some embodiments the amount of peptide is no more than 15% (w/w) or no more than 10% (w/w), such as 1-5% (w/w). In some embodiments the peptide is in the intragranular part of the composition.

In some embodiments the composition of the invention comprises a GLP-1 peptide. The term "GLP-1 peptide" as used herein refers to a compound, which fully or partially activates the human GLP-1 receptor. In some embodiments the "GLP-1 peptide" binds to a GLP-1 receptor, e.g., with an affinity constant ($K_D$) or activate the receptor with a potency ($EC_{50}$) of below 1 µM, e.g. below 100 nM as measured by methods known in the art (see e.g. WO98/08871) and exhibits insulinotropic activity, where insulinotropic activity may be measured in vivo or in vitro assays known to those of ordinary skill in the art. For example, the GLP-1 peptide may be administered to an animal with increased blood glucose (e.g. obtained using an Intravenous Glucose Tolerance Test (IVGTT), a person skilled in the art will be able to determine a suitable glucose dosage and a suitable blood sampling regime, e.g. depending on the species of the animal, for the IVGTT) and the plasma insulin concentration measured over time.

In some embodiments the GLP-1 peptide is a GLP-1 analogue, optionally comprising one substituent. The term "analogue" as used herein referring to a GLP-1 peptide (hereafter "peptide") means a peptide wherein at least one amino acid residue of the peptide has been substituted with another amino acid residue and/or wherein at least one amino acid residue has been deleted from the peptide and/or wherein at least one amino acid residue has been added to the peptide and/or wherein at least one amino acid residue of the peptide has been modified. Such addition or deletion of amino acid residues may take place at the N-terminal of the peptide and/or at the C-terminal of the peptide. In some embodiments a simple nomenclature is used to describe the GLP-1 peptide, e.g., [Aib8] GLP-1(7-37) designates an analogue of GLP-1(7-37) wherein the naturally occurring Ala in position 8 has been substituted with Aib. In some embodiments the GLP-1 peptide comprises a maximum of twelve, such as a maximum of 10, 8 or 6, amino acids which have been alterered, e.g., by substitution, deletion, insertion and/or modification, compared to e.g. GLP-1(7-37). In some embodiments the analogue comprises up to 10 substitutions, deletions, additions and/or insertions, such as up to 9 substitutions, deletions, additions and/or insertions, up to 8 substitutions, deletions, additions and/or insertions, up to 7 substitutions, deletions, additions and/or insertions, up to 6 substitutions, deletions, additions and/or insertions, up to 5 substitutions, deletions, additions and/or insertions, up to 4 substitutions, deletions, additions and/or insertions or up to 3 substitutions, deletions, additions and/or insertions, compared to e.g. GLP-1(7-37). Unless otherwise stated the GLP-1 comprises only L-amino acids.

In some embodiments the term "GLP-1 analogue" or "analogue of GLP-1" as used herein refers to a peptide, or a compound, which is a variant of the human Glucagon-Like Peptide-1 (GLP-1(7-37)). GLP-1(7-37) has the sequence HAEGTFTSDV SSYLEGQAAKEFIAWLVKGRG (SEQ ID No: 1). In some embodiments the term "variant" refers to a compound which comprises one or more amino acid substitutions, deletions, additions and/or insertions.

In some embodiments the GLP-1 peptide exhibits at least 60%, 65%, 70%, 80% or 90% sequence identity to GLP-1 (7-37) over the entire length of GLP-1(7-37). As an example of a method for determination of sequence identity between two analogues the two peptides [Aib8]GLP-1(7-37) and GLP-1(7-37) are aligned. The sequence identity of [Aib8] GLP-1(7-37) relative to GLP-1(7-37) is given by the number of aligned identical residues minus the number of different residues divided by the total number of residues in GLP-1 (7-37). Accordingly, in said example the sequence identity is (31-1)/31.

In some embodiments the C-terminal of the GLP-1 peptide is an amide.

In some embodiments the GLP-1 peptide is GLP-1(7-37) or GLP-1(7-36)amide. In some embodiments the GLP-1 peptide is exendin-4, the sequence of which is HGEGTFITSDLSKQMEEEAVRLFIEWLKNGGPSSGAPPPS (SEQ ID No: 2).

In some embodiments the GLP-1 peptide comprises one substituent which is covalently attached to the peptide. In some embodiments the substituent comprises a fatty acid or a fatty diacid. In some embodiments the substituent comprises a C16, C18 or C20 fatty acid. In some embodiments the substituent comprises a C16, C18 or C20 fatty diacid. In some embodiments the substituent comprises formula (X)

wherein n is at least 13, such as n is 13, 14, 15, 16, 17, 18 or 19. In some embodiments the substituent comprises formula (X), wherein n is in the range of 13 to 19, such as in the range of 13 to 17. In some embodiments the substituent comprises formula (X), wherein n is 13, 15 or 17. In some embodiments the substituent comprises formula (X), wherein n is 13. In some embodiments the substituent comprises formula (X), wherein n is 15. In some embodiments the substituent comprises formula (X), wherein n is 17. In some embodiments the substituent comprises one or more 8-amino-3,6-dioxaoctanoic acid (OEG), such as two OEG.

In some embodiments the substituent is [2-(2-{2-[2-(2-{2-[(S)-4-carboxy-4-(17-carboxyheptadecanoylamino)butyrylamino]ethoxy}ethoxy)acetylamino]ethoxy}ethoxy)acetyl].

In some embodiments the substituent is [2-(2-{2-[2-(2-{2-[(S)-4-carboxy-4-({trans-4-[(19-carboxynonadecanoylamino)methyl]cyclohexanecarbonyl}amino)butyrylamino]ethoxy}-ethoxy)acetylamino]ethoxy}ethoxy)acetyl].

In some embodiments the GLP-1 peptide is semaglutide, also known as N-epsilon26-[2-(2-{2-[2-(2-{2-[(S)-4-carboxy-4-(17-carboxyheptadecanoylamino)butyrylamino]-ethoxy}ethoxy)acetylamino]ethoxy}ethoxy)acetyl][Aib8,Arg34]GLP-1(7-37), which may be prepared as described in WO2006/097537, Example 4.

In some embodiments the composition comprises the GLP-1 peptide or a pharmaceutically acceptable salt, amide, or ester thereof. In some embodiments the composition comprises the GLP-1 peptide one or more pharmaceutically acceptable counter ions.

In some embodiments the dosage of GLP-1 is in the range of 0.01 mg to 100 mg. In some embodiments the composition or granulate comprises an amount of a GLP-1 peptide in the range of at least 1 mg, such as at least 5 mg or at least 10 mg. In some embodiments the composition or granulate comprises 10 mg GLP-1 peptide.

In some embodiments the composition comprises an amount of a GLP-1 peptide in the range of 0.05 to 25 μmol, such as in the range of 0.5 to 20 μmol.

In some embodiments the GLP-1 peptide is selected from one or more of the GLP-1 peptides mentioned in WO93/19175, WO96/29342, WO98/08871, WO99/43707, WO99/43706, WO99/43341, WO99/43708, WO2005/027978, WO2005/058954, WO2005/058958, WO2006/005667, WO2006/037810, WO2006/037811, WO2006/097537, WO2006/097538, WO2008/023050, WO2009/030738, WO2009/030771 and WO2009/030774.

In some embodiments the GLP-1 peptide is selected from the group consisting of N-epsilon37{2-[2-(2-{2-[2-((R)-3-carboxy-3-{[1-(19-carboxynonadecanoyl)piperidine-4-carbonyl]amino}propionylamino)ethoxy]ethoxy}acetylamino)ethoxy]ethoxy}acetyl-[desaminoHis7,Glu22,Arg26,Arg34,Lys37]GLP-1(7-37)amide; N-epsilon26{2-[2-(2-{2-[2-((R)-3-carboxy-3-{[1-(19-carboxynonadecanoyl)piperidine-4-carbonyl]amino}propionylamino)-ethoxy]ethoxy}acetylamino)ethoxy]ethoxy}acetyl[desaminoHis7,Arg34]GLP-1-(7-37); N-epsilon37{2-[2-(2-{2-[2-((S)-3-carboxy-3-{[1-(19-carboxy-nonadecanoyl)piperidine-4-carbonyl]amino}propionylamino)ethoxy]ethoxy}acetylamino)ethoxy]ethoxy}acetyl-[Aib8,Glu22,Arg26,Arg34,Lys37]GLP-1-(7-37)amide; N-epsilon37-[2-(2-[2-(2-[2-(2-((R)-3-[1-(17-carboxyheptadecanoyl)piperidin-4-ylcarbonylamino]3-carboxypropionylamino)ethoxy)-ethoxy]acetylamino)ethoxy]ethoxy)acetyl][DesaminoHis7,Glu22,Arg26,Arg34,Phe(m-CF3)28]GLP-1-(7-37)amide; N-epsilon26-[(S)-4-carboxy-4-({trans-4-[(19-carboxy-nonadecanoylamino)methyl]cyclohexanecarbonyl}amino)butyryl][Aib8,Arg34]GLP-1-(7-37); N-epsilon26-{4-[(S)-4-carboxy-4-({trans-4-[(19-carboxynonadecanoylamino)methyl]-cyclohexanecarbonyl}amino)butyrylamino]butyryl}[Aib8,Arg34]GLP-1-(7-37); N-epsilon26-[2-(2-{2-[(S)-4-carboxy-4-({trans-4-[(19-carboxy-nonadecanoylamino)methyl]cyclohexane-carbonyl}amino)butyrylamino]ethoxy}ethoxy)acetyl][Aib8,Arg34]GLP-1-(7-37); N-epsilon26-[2-(2-{2-[2-(2-{2-[(S)-4-carboxy-4-({trans-4-[(19-carboxy-nonadecanoylamino)methyl]-cyclohexanecarbonyl}amino)butyrylamino]ethoxy}ethoxy)acetylamino]ethoxy}ethoxy)acetyl]-[Aib8,Arg34]GLP-1-(7-37)amide; N-epsilon37-[2-(2-{2-[2-(2-{2-[(S)-4-carboxy-4-({trans-4-[(19-carboxy-nonadecanoylamino)methyl]cyclohexanecarbonyl}amino)butyrylamino]ethoxy}-ethoxy)acetylamino]ethoxy}ethoxy)acetyl][Aib8,Glu22,Arg26,Arg34,Lys37]GLP-1-(7-37)amide; N-epsilon37-[2-(2-{2-[2-(2-{2-[(S)-4-carboxy-4-({trans-4-[(19-carboxy-nonadecanoylamino)methyl]cyclohexanecarbonyl}amino)butyrylamino]ethoxy}ethoxy)-acetylamino]ethoxy}ethoxy)acetyl][DesaminoHis7,Glu22,Arg26,Arg34,Lys37]GLP-1-(7-37) amide; N-epsilon37-[2-(2-{2-[2-(2-{2-[(S)-4-carboxy-4-({4-[(trans-19-carboxy-nonadecanoylamino)methyl]cyclohexanecarbonyl}amino)butyrylamino]ethoxy}ethoxy)-acetylamino]ethoxy}ethoxy)acetyl][DesaminoHis7,Arg26,Arg34,Lys37]GLP-1-(7-37)amide; N-epsilon37-[2-(2-{2-[2-(2-{2-[(S)-4-carboxy-4-({trans-4-[(19-carboxy-nonadecanoylamino)-methyl]cyclohexanecarbonyl}amino)butyrylamino]ethoxy}ethoxy)acetylamino]ethoxy}ethoxy)-acetyl][DesaminoHis7,Glu22,Arg26,Arg34,Lys37]GLP-1-(7-37); N-epsilon26[2-(2-{2-[2-(2-{2-[(S)-4-carboxy-4-({4-[(19-carboxy-nonadecanoylamino)methyl]cyclohexanecarbonyl}amino)-butyrylamino]ethoxy}ethoxy)acetylamino]ethoxy}ethoxy)acetyl[Aib8,Lys26]GLP-1 (7-37)amide; N-epsilon26 [2-(2-[2-(2-(2-((S)-2-[trans-4-((9-carboxynonadecanoylamino]-methyl)cyclohexylcarbonylamino]-4-carboxybutanoylamino)

ethoxy)ethoxy]acetylamino)-ethoxy]ethoxy)acetyl][Aib8, Lys26]GLP-1 (7-37)amide; N-epsilon37-[2-(2-{2-[2-(2-{2-[(S)-4-carboxy-4-({trans-4-[(19-carboxy-nonadecanoylamino)methyl]cyclohexane-carbonyl} amino) butyrylamino]ethoxy}ethoxy)acetylamino]ethoxy}ethoxy) acetyl][DesaminoHis7,Arg26,Arg34,Lys37]GLP-1-(7-37); N-epsilon37-[2-(2-{2-[2-(2-{2-[(S)-4-carboxy-4-({trans-4-[(19-carboxy-nonadecanoylamino)methyl]cyclohexanecarbonyl} amino)butyrylamino]ethoxy}ethoxy)acetylamino] ethoxy}ethoxy)acetyl][DesaminoHis7,Glu22, Arg26,Glu30, Arg34,Lys37]GLP-1-(7-37); N-epsilon26-[2-(2-{2-[(S)-4-carboxy-4-((S)-4-carboxy-4-{4-[4-(16-(1H-tetrazol-5-yl)-hexadecanoylsulfamoyl)butyrylamino]-butyrylamino}butyrylamino) butyrylamino]ethoxy}ethoxy) acetyl][Aib8,Arg34]GLP-1-(7-37); N-epsilon26-[2-(2-{2-[(S)-4-carboxy-4-((S)-4-carboxy-4-{12-[4-(16-(1H-tetrazol-5-yl)hexadecanoyl-sulfamoyl)butyrylamino] dodecanoylamino}butyrylamino) butyrylamino] ethoxy}ethoxy)acetyl][Aib8,Arg34]GLP-1-(7-37); N-epsilon26-[2-(2-{2-[(S)-4-carboxy-4-((S)-4-carboxy-4-{6-[4-(16-(1H-tetrazol-5-yl)hexadecanoyl-sulfamoyl)butyrylamino]hexanoylamino} butyrylamino)butyrylamino]ethoxy}ethoxy) acetyl][Aib8,Arg34]GLP-1-(7-37); N-epsilon26-[2-(2-{2-[(S)-4-carboxy-4-((S)-4-carboxy-4-{4-[4-(16-(1H-tetrazol-5-yl)hexadecanoylsulfamoyl)butyrylamino]butyrylamino}butyrylamino)butyrylamino]ethoxy}ethoxy)acetyl][Aib8,Arg34]GLP-1-(7-34); N-epsilon26-[2-(2-{2-[(S)-4-carboxy-4-((S)-4-carboxy-4-{12-[4-(16-(1H-tetrazol-5-yl)hexadecanoylsulfamoyl)butyrylamino]-dodecanoylamino}butyrylamino) butyrylamino]ethoxy}ethoxy)acetyl][Aib8,Arg34]GLP-1-(7-34); N-epsilon26-[2-(2-{2-[(S)-4-carboxy-4-((S)-4-carboxy-4-{6-[4-(16-(1H-tetrazol-5-yl)hexadecanoylsulfamoyl) butyrylamino]hexanoylamino}butyrylamino) butyrylamino]ethoxy}ethoxy)acetyl][Aib8,Arg34]GLP-1-(7-34); N-epsilon26-[2-(2-{2-[(S)-4-carboxy-4-((S)-4-carboxy-4-{12-[4-(16-(1H-tetrazol-5-yl)hexadecanoyl-sulfamoyl)butyrylamino]dodecanoylamino} butyrylamino)butyrylamino]ethoxy}ethoxy)acetyl][Aib8,Arg34]GLP-1-(7-35); N-epsilon26-[2-(2-{2-[(S)-4-carboxy-4-((S)-4-carboxy-4-{6-[4-(16-(1H-tetrazol-5-yl)hexadecanoylsulfamoyl)butyrylamino]hexanoylamino} butyrylamino)butyrylamino]ethoxy}ethoxy)acetyl][Aib8,Arg34]GLP-1-(7-35); N-epsilon26-[2-(2-{2-[(S)-4-carboxy-4-((S)-4-carboxy-4-{6-[4-(16-(1H-tetrazol-5-yl)hexadecanoylsulfamoyl)butyrylamino]hexanoylamino}butyrylamino)butyrylamino]ethoxy}ethoxy)acetyl][Aib8,Arg34]GLP-1-(7-36)amide; N-epsilon26-[2-(2-{2-[(S)-4-carboxy-4-((S)-4-carboxy-4-{6-[4-(16-(1H-tetrazol-5-yl)hexadecanoylsulfamoyl) butyrylamino]hexanoylamino}butyrylamino) butyrylamino]ethoxy}ethoxy)acetyl][Aib8,Arg34]GLP-1-(7-35); N-epsilon26-[2-(2-{2-[(S)-4-carboxy-4-((S)-4-carboxy-4-{12-[4-(16-(1H-tetrazol-5-yl)hexadecanoyl-sulfamoyl)butyrylamino]dodecanoylamino}butyryl-amino)butyrylamino]ethoxy} ethoxy)acetyl][Aib8,Lys33,Arg34]GLP-1-(7-34); N-epsilon26-[2-(2-{2-[(S)-4-carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Arg34]GLP-1-(7-36)amide; N-epsilon26-[2-(2-{2-[2-(2-{2-[2-(2-{2-[2-(2-{2-[2-(2-{2-[2-(2-{(S)-4-carboxy-4-((S)-4-carboxy-4-{12-[4-(16-(1H-tetrazol-5-yl)hexadecanoylsulfamoyl) butyrylamino] dodecanoylamino}butyrylamino) butyrylamino] ethoxy}ethoxy) acetylamino]ethoxy}ethoxy)acetylamino] ethoxy}ethoxy)acetylamino]ethoxy}ethoxy)acetyl][Aib8, Lys26,Arg34]GLP-1-(7-36)amide; N-epsilon37-[2-(2-{2-[(S)-4-carboxy-4-((S)-4-carboxy-4-{12-[4-(16-(1H-tetrazol-5-yl)hexadecanoylsulfamoyl)butyrylamino] dodecanoylamino}butyrylamino) butyrylamino] ethoxy}ethoxy)acetyl][Aib8,Glu22,Arg26,Arg34,Lys37] GLP-1-(7-37)amide; N-epsilon37-[2-(2-{2-[(S)-4-carboxy-4-((S)-4-carboxy-4-{12-[4-(16-(1H-tetrazol-5-yl) hexadecanoylsulfamoyl)butyrylamino] dodecanoylamino}butyrylamino) butyrylamino] ethoxy}ethoxy)acetyl][DesaminoHis7,Glu22,Arg26,Arg34, Lys37]GLP-1-(7-37)amide; N-epsilon37{2-[2-(2-{2-[2-((R)-3-carboxy-3-{[1-(19-carboxy-nonadecanoyl) piperidine-4-carbonyl]amino}propionylamino)ethoxy]ethoxy} acetylamino)ethoxy] ethoxy}acetyl [desaminoHis7,Glu22, Arg26,Arg34,Lys37]GLP-1(7-37)amide; N-epsilon37{2-[2-(2-{2-[2-((S)-3-carboxy-3-{[1-(19-carboxynonadecanoyl) piperidine-4-carbonyl]amino} propionylamino) ethoxy] ethoxy}acetylamino)ethoxy] ethoxy} acetyl [Aib8,Glu22, Arg26,Arg34, Lys37]GLP-1-(7-37)amide; N-epsilon37-[2-(2-[2-[2-[2-((R)-3-[1-(17-carboxyhepta-decanoyl)piperidin-4-ylcarbonylamino]3-carboxy-propionylamino) ethoxy) ethoxy] acetylamino) ethoxy] ethoxy)acetyl] [DesaminoHis7, Glu22,Arg26, Arg34,Phe(m-CF3)28] GLP-1-(7-37)amide; N-epsilon37-[2-(2-{2-[2-(2-{2-[(S)-4-carboxy-4-({trans-4-[(19-carboxy-nonadecanoylamino) methyl] cyclohexanecarbonyl} amino)butyrylamino] ethoxy} ethoxy)acetylamino] ethoxy}ethoxy)acetyl] [Aib8, Glu22,Arg26,Arg34,Lys37]GLP-1-(7-37)amide; N-epsilon37-[2-(2-{2-[2-(2-{2-[(S)-4-carboxy-4-({trans-4-[(19-carboxy-nonadecanoylamino)methyl]cyclohexane-carbonyl} amino)butyrylamino]ethoxy}ethoxy) acetylamino] ethoxy}ethoxy)acetyl] [DesaminoHis7,Glu22,Arg26, Arg34,Lys37]GLP-1-(7-37)amide; N-epsilon37-[2-(2-{2-[2-(2-{2-[(S)-4-carboxy-4-({trans-4-[(19-carboxy-nonadecanoylamino)methyl] cyclohexanecarbonyl}amino) butyrylamino]ethoxy}ethoxy) acetylamino]ethoxy} ethoxy) acetyl] [DesaminoHis7,Glu22,Arg26, Arg34, Lys37]GLP-1-(7-37); N-epsilon37-[2-(2-{2-[2-(2-{2-[(S)-4-carboxy-4-({trans-4-[(19-carboxy-nonadecanoylamino) methyl] cyclohexane-carbonyl}amino)butyrylamino] ethoxy}ethoxy) acetylamino] ethoxy}ethoxy)acetyl] [DesaminoHis7,Glu22,Arg26,Glu30,Arg34, Lys37]GLP-1-(7-37); N-epsilon37-[2-(2-{2-[(S)-4-carboxy-4-((S)-4-carboxy-4-{12-[4-(16-(1H-tetrazol-5-yl)hexadecanoyl-sulfamoyl) butyrylamino]dodecanoylamino} butyrylamino) butyrylamino] ethoxy}ethoxy)acetyl] [Aib8,Glu22,Arg26, Arg34,Lys37]GLP-1-(7-37)amide; N-epsilon37-[2-(2-{2-[(S)-4-carboxy-4-((S)-4-carboxy-4-{12-[4-(16-(1H-tetrazol-5-yl)hexadecanoylsulfamoyl) butyrylamino] dodecanoylamino}butyrylamino) butyrylamino] ethoxy}ethoxy)acetyl] [DesaminoHis7,Glu22,Arg26, Arg34,Lys37]GLP-1-(7-37)amide; N-epsilon37-(3-((2-(2-(2-(2-(2-Hexadecyloxyethoxy)ethoxy)ethoxy) ethoxy) ethoxy)) propionyl)[DesaminoHis7,Glu22,Arg26,Arg34, Lys37]GLP-1(7-37)-amide; N-epsilon37-{2-(2-(2-(2-[2-(2-(4-(hexadecanoylamino)-4-carboxybutyryl-amino)ethoxy) ethoxy] acetyl)ethoxy)ethoxy)acetyl)}-[desaminoHis7, Glu22,Arg26, Glu30,Arg34,Lys37] GLP-1-(7-37)amide; N-epsilon37-{2-(2-(2-(2-[2-(2-(4-(hexadecanoylamino)-4-carboxy-butyryl-amino) ethoxy)ethoxy]acetyl)ethoxy) ethoxy) acetyl)}-[desaminoHis7,Glu22, Arg26, Arg34, Lys37]GLP-1-(7-37)amide; N-epsilon37-(2-(2-(2-(2-(2-(2-(2-(2-(octadecanoyl-amino)ethoxy)ethoxy) acetylamino) ethoxy) ethoxy)acetylamino) ethoxy)ethoxy) acetyl) [desaminoHis7,Glu22,Arg26,Arg34,Lys37] GLP-1 (7-37) amide; N-epsilon37-[4-(16-(1H-Tetrazol-5-yl) hexadecanoylsulfamoyl) butyryl] [DesaminoHis7,Glu22, Arg26, Arg34, Lys37]GLP-1-(7-37)amide; N-epsilon37-[2-(2-{2-[2-(2-{2-[(S)-4-carboxy-4-(19-carboxynonadecanoylamino) butyrylamino] ethoxy}ethoxy) acetylamino] ethoxy} ethoxy)acetyl] [DesaminoHis7,Glu22,Arg26, Arg34,Lys37]GLP-1-(7-37); N-epsilon37-(2-{2-[2-((S)-4-carboxy-4-{(S)-4-carboxy-4-[(S)-4-carboxy-4-(19-carboxynonadecanoylamino)butyrylamino]butyrylamino} butyrylamino)ethoxy]ethoxy} acetyl)[DesaminoHis7,Glu22, Arg26,Arg34,Lys37]GLP-1-(7-37); N-epsilon37-{2-[2-(2-{(S)-4-[(S)-4-(12-{4-[16-(2-tert-Butyl-2H-tetrazol-5-yl)-hexadecanoylsulfamoyl] butyrylamino}dodecanoylamino)-4-carboxybutyrylamino]-4-carboxybutyrylamino} ethoxy)ethoxy]acetyl}[DesaminoHis7,Glu22,Arg26,Arg34,Lys37] GLP-1 (7-37); N-epsilon37-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] [Aib8,Glu22, Arg26,Arg34,Lys37]GLP-1-(7-37); N-alpha37-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] [Aib8,Glu22,Arg26, Arg34,epsilon-Lys37]GLP-1-(7-37)peptide; N-epsilon37-[2-(2-[2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] [desaminoHis7, Glu22,Arg26,Arg34,Lys37] GLP-1-(7-37); N-epsilon36-[2-(2-{2-[2-(2-{2-[(S)-4-carboxy-4-(15-carboxy-pentadecanoylamino)-butyrylamino]-ethoxy}-ethoxy)-acetylamino]-ethoxy}-ethoxy)-acetyl] [desaminoHis7, Glu22, Arg26,Glu30,Arg34,Lys36] GLP-1-(7-37)-Glu-Lys peptide; N-epsilon37-[2-(2-{2-[2-(2-{2-[(S)-4-carboxy-4-({trans-4-[(19-carboxynonadecanoylamino)methyl] cyclohexanecarbonyl}amino)butyryl-amino] ethoxy}ethoxy)acetylamino]ethoxy}ethoxy)acetyl][Aib8, Glu22,Arg26,Arg34,Lys37]GLP-1-(7-37); N-epsilon37-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylHAib8,Glu22, Arg26, Arg34,Aib35,Lys37]GLP-1-(7-37); N-epsilon37-[(S)-4-carboxy-4-(2-{2-[2-(2-{2-[2-(17-carboxyheptadecanoylamino) ethoxy] ethoxy} acetylamino) ethoxy] ethoxy} acetylamino) butyryl] [Aib8,Glu22,Arg26, 34,Lys37] GLP-1 (7-37); N-epsilon37-[2-(2-[2-(2-[2-(2-[4-(17-carboxyheptadecanoylamino)-4(S)-carboxybutyrylamino]ethoxy)ethoxy]acetylamino)ethoxy]ethoxy)acetyl] [ImPr7,Glu22, Arg26,34,Lys37], GLP-1-(7-37); N-epsilon26-{2-[2-(2-{2-[2-(2-{(S)-4-carboxy-4-[10-(4-carboxy-phenoxy) decanoylamino]butyrylamino}ethoxy)ethoxy] acetylamino}ethoxy) ethoxy]acetyl}, N-epsilon37-{2-[2-(2-{2-[2-(2-{(S)-4-carboxy-4-[10-(4-carboxy-phenoxy) decanoylamino] butyrylamino}ethoxy)ethoxy] acetylamino}ethoxy) ethoxy]acetyl}-[Aib8,Arg34,Lys37] GLP-1(7-37)-OH; N-epsilon26 (17-carboxyhepta-decanoyl)-[Aib8,Arg34]GLP-1-(7-37)-peptide; N-epsilon26-(19-carboxynonadecanoyl)-[Aib8,Arg34]GLP-1-(7-37); N-epsilon26-(4-{[N-(2-carboxyethyl)-N-(15-carboxypentadecanoyl)amino]methyl}benzoyl[Arg34]GLP-1-(7-37); N-epsilon26-[2-(2-[2-(2-[2-(2-[4-(17-carboxyheptadecanoylamino)-4(S)-carboxybutyrylamino]ethoxy)ethoxy]acetylamino) ethoxy]ethoxy)acetyl][Aib8,Arg34]GLP-1-(7-37); N-epsilon26-[2-(2-[2-(2-[2-(2-[4-(19-carboxynonadecanoylamino)-4(S)-carboxybutyrylamino]ethoxy)ethoxy]acetylamino)ethoxy]ethoxy)acetyl][Aib8,Arg34]GLP-1-(7-37); N-epsilon26-[2-(2-[2-(2-[2-(2-[4-(17-carboxyheptadecanoylamino)-4(S)-carboxybutyrylamino]ethoxy)ethoxy]acetylamino)ethoxy]ethoxy)acetyl][3-(4-Imidazolyl)Propionyl7,Arg34]GLP-1-(7-37); N-epsilon26-[2-(2-[2-(2-[2-(2-[4-(17-carboxyheptadecanoylamino)-(carboxymethyl-amino)acetylamino]ethoxy)ethoxy]acetylamino)ethoxy]ethoxy)acetyl][Aib8,Arg34]GLP-1-(7-37); N-epsilon26-[2-(2-[2-(2-[2-(2-[4-(17-carboxyheptadecanoylamino)-3(S)-Sulfopropionylamino]ethoxy)ethoxy]acetylamino)ethoxy]ethoxy)acetyl][Aib8,Arg34]GLP-1-(7-37); N-epsilon26-[2-(2-[2-(2-[2-(2-[4-(17-carboxyheptadecanoylamino)-4(S)-carboxybutyrylamino]ethoxy)ethoxy]acetylamino)ethoxy]ethoxy)acetyl][Gly8,Arg34] GLP-1-(7-37); N-epsilon26-[2-(2-[2-(2-[2-(2-[4-(17-carboxyheptadecanoylamino)-4(S)-carboxybutyrylamino]ethoxy)ethoxy]acetylamino)ethoxy]ethoxy)acetyl][Aib8,Arg34]GLP-1-(7-37)-amide; N-epsilon26-[2-(2-[2-(2-[2-(2-[4-(17-carboxyheptadecanoylamino)-4(S)-carboxybutyrylamino]ethoxy)ethoxy]acetylamino)ethoxy]ethoxy)acetyl] [Aib8,Arg34,Pro37]GLP-1-(7-37)amide; Aib8,Lys26(N-epsilon26-{2-(2-(2-(2-[2-(2-(4-(pentadecanoylamino)-4-carboxybutyrylamino) ethoxy)ethoxy]acetyl)ethoxy) ethoxy)acetyl)}), Arg34) GLP-1 H(7-37)-OH; N-epsilon26-[2-(2-[2-(2-[2-(2-[4-{[N-(2-carboxyethyl)-N-(17-carboxyheptadecanoyl)amino] methyl}benzoyl)amino]ethoxy) ethoxy]acetylamino) ethoxy]ethoxy)acetyl][Aib8,Arg34]GLP-1(7-37); N-alpha7-formyl, N-epsilon26-[2-(2-[2-(2-[2-(2-[4-(17-carboxyheptadecanoyl-amino)-4(S)-carboxy-butyrylamino] ethoxy)ethoxy]acetylamino)ethoxy]ethoxy)acetyl] [Arg34] GLP-1-(7-37); N-epsilon2626-[2-(2-[2-(2-[2-(2-[4-(17-carboxyheptadecanoylamino)-4(S)-carboxy-butyrylamino] ethoxy)ethoxy]acetylamino)ethoxy]ethoxy)acetyl][Aib8, Glu22, Arg34] GLP-1-(7-37); N-epsilon26{3-[2-(2-{2-[2-(2-{2-[2-(2-[4-(15-(N-((S)-1,3-dicarboxypropyl) carbamoyl)pentadecanoylamino)-(S)-4-carboxybutyrylamino] ethoxy)ethoxy] ethoxy}ethoxy)ethoxy]ethoxy}ethoxy) ethoxy]propionyl} [Aib8,Arg34]GLP-1-(7-37); N-epsilon26-[2-(2-[2-(2-[2-(2-[4-{[N-(2-carboxyethyl)-N-(17-carboxy-heptadecanoyl)amino]methyl}benzoyl)amino](4(S)-carboxybutyryl-amino)ethoxy) ethoxy]acetylamino)ethoxy]acetyl][Aib8,Arg34] GLP-1(7-37); N-epsilon26-{(S)-4-carboxy-4-((S)-4-carboxy-4-((S)-4-carboxy-4-((S)-4-carboxy-4-(19-carboxy-nonadecanoylamino)butyrylamino) butyrylamino)butyrylamino) butyrylamino} [Aib8,Arg34] GLP-1-(7-37); N-epsilon26-4-(17-carboxyheptadecanoyl-amino)-4(S)-carboxybutyryl-[Aib8,Arg34]GLP-1-(7-37); N-epsilon26-{3-[2-(2-{2-[2-(2-{2-[2-(2-[4-(17-carboxy-heptadecanoylamino)-4(S)-carboxybutyrylamino]ethoxy) ethoxy]ethoxy} ethoxy)ethoxy[ethoxy}ethoxy)ethoxy]propionyl][Aib8,Arg34]GLP-1-(7-37); N-epsilon26-{2-(2-(2-(2-[2-(2-(4-(17-carboxyheptadecanoylamino)-4-carboxybutyrylamino) ethoxy)ethoxy]acetyl)ethoxy) ethoxy)acetyl)}[Aib8,22,27,30,35,Arg34,Pro37, Lys26] GLP-1 (7-37)amide; N-epsilon26-[2-(2-[2-[4-(21-carboxyuneicosanoylamino)-4(S)-carboxybutyrylamino]ethoxy] ethoxy)acetyl][Aib8,Arg34]GLP-1-(7-37); and N-epsilon26-[2-(2-[2-(2-[2-(2-[4-(21-carboxyuneicosanoylamino)-4(S)-carboxybutyrylamino] ethoxy)ethoxy]acetylamino)ethoxy]ethoxy)acetyl][Aib8, Arg34]GLP-1-(7-37).

In some embodiments the GLP-1 peptide is N-epsilon26-[2-(2-{2-[2-(2-{2-[(S)-4-carboxy-4-(17-carboxyheptadecanoylamino)butyrylamino]ethoxy}ethoxy)acetylamino]-ethoxy}ethoxy)acetyl][Aib8,Arg34]GLP-1(7-37), also known as semaglutide.

Salt of NAC

The delivery agent used in the present invention is a salt of N-(8-(2-hydroxybenzoyl)amino)caprylic acid (NAC). In some embodiments the delivery agent is an absorption enhancer. The structural formula of N-(8-(2-hydroxybenzoyl)amino)caprylate is shown in formula (I).

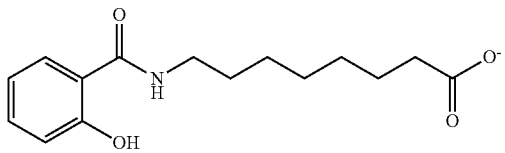

In some embodiments the amount of salt of NAC is at least 50% (w/w) or at least 60% (w/w), such as 50-90% (w/w), 55-85% (w/w) or 70-80% (w/w), or such as 65-75% (w/w), 60-80% (w/w), or 50-90% (w/w). In some embodiments the salt of NAC is in the intragranular part of the composition.

In some embodiments the salt of NAC comprises one monovalent cation, two monovalent cations or one divalent cation. In some embodiments the salt of NAC is selected from the group consisting of the sodium salt, potassium salt and calcium salt of NAC.

The salts of NAC may be prepared using the method described in e.g. WO96/030036, WO00/046182, WO01/092206 or WO2008/028859.

The salt of NAC may be crystalline and/or amorphous. In some embodiments the delivery agent comprises any hydrate, solvate and/or anhydrate form of the salt of NAC, such as the anhydrate, monohydrate, dihydrate, trihydrate, a solvate or one third of a hydrate of the salt of N-(8-(2-hydroxybenzoyl)amino) caprylic acid as well as combinations thereof. In some embodiments the delivery agent is a salt of NAC as described in WO2007/121318.

In some embodiments the delivery agent is sodium NAC (referred to as "SNAC" herein), also known as sodium 8-(salicyloylamino)octanoate.

In some embodiments the amount of the salt of N-(8-(2-hydroxybenzoyl)amino)-caprylic acid in the composition is in the range of 0.6-3.5 mmol. In some embodiments the amount of the salt of N-(8-(2-hydroxybenzoyl)amino) caprylic acid in the composition is at least 0.6 mmol, such as selected from the group at least 0.8 mmol or at least 0.9 mmol. In some embodiments the amount of the salt of NAC in the composition is up to 2.5 mmol. In some embodiments the amount of the salt of NAC is 1 mmol, such as 1.08 mmol.

In some embodiments the amount of SNAC in the composition is in the range of 100-1000 mg. In some embodiments the amount of SNAC in the composition is at least 150 mg, such as or at least 250 mg. In some embodiments the amount of SNAC in the composition is up to 800 mg, such as up to 700 mg or up to 600 mg. In some embodiments the amount of SNAC in the composition is 300 mg.

In some embodiments the molar ratio between the peptide and the salt of NAC in the tablet is 1:10 or more, i.e. the salt of NAC is in 10 fold excess of the peptide or more when measured in moles, such as 1:50 or more, or 1:100 or more.

Method of Controlling Tablet Porosity

In some embodiments the invention relates to a method for controlling porosity of a group of tablets, said method comprising the steps of: a) determining the near-infrared (NIR) spectrum of a selection of tablets, b) comparing said spectrum to a reference NIR spectrum or performing a statistical analysis of said spectrum to determine the tablet porosity, and c) selecting a subgroup of tablets with a NIR spectrum or porosity within a predetermined range. In some embodiments said method for controlling porosity is an at-line NIR method. As used herein, the term "at-line NIR method" is intended to mean a method wherein a NIR spectrometer is placed next to tabletting press and measurement needs an operator to remove and analyse tablets. In some embodiments said method for controlling porosity is an in-line NIR method. As used herein, the term "in-line NIR method" is intended to mean a method wherein a NIR spectrometer is attached to the tabletting press and measurement is performed automatically. In some embodiments said method for controlling porosity comprises continuous measurement of porosity. In some embodiments said method for controlling porosity comprises comparison of said spectrum to a reference spectrum. In some embodiments said method for controlling porosity comprises adjustment of tabletting parameters during tabletting in order to improve the porosity of the tablets. In some embodiments said method for controlling porosity comprises obtaining a subgroup of tablets with the desired porosity. In some embodiments said method for controlling porosity said tablet is as defined herein. In some embodiments the term "a group of tablets" is intended to mean at least two tablets, such as at least 10 tablets, 5-100 or 20-50 tablets.

Pharmaceutical Indications

The present invention also relates to a composition or a granulate of the invention for use as a medicament. In some embodiments the composition or the granulate is administered orally.

In particular embodiments, the composition or a granulate of the invention may be used for the following medical treatments, all preferably relating one way or the other to diabetes:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying;

(vi) prevention and/or treatment of diabetic complications, such as neuropathy, including peripheral neuropathy; nephropathy; or retinopathy;

(vii) improving lipid parameters, such as prevention and/or treatment of dyslipidemia, lowering total serum lipids; lowering HDL; lowering small, dense LDL; lowering VLDL: lowering triglycerides; lowering cholesterol; increasing HDL; lowering plasma levels of lipoprotein a (Lp(a)) in a human; inhibiting generation of apolipoprotein a (apo(a)) in vitro and/or in vivo;

(iix) prevention and/or treatment of cardiovascular diseases, such as syndrome X; atherosclerosis; myocardial infarction; coronary heart disease; stroke, cerebral ischemia; an early cardiac or early cardiovascular disease, such as left ventricular hypertrophy; coronary artery disease; essential hypertension; acute hypertensive emergency; cardiomyopathy; heart insufficiency; exercise tolerance; chronic heart failure; arrhythmia; cardiac dysrhythmia; syncopy; atheroschlerosis; mild chronic heart failure; angina pectoris; cardiac bypass reocclusion; intermittent claudication (atheroschlerosis oblitterens); diastolic dysfunction; and/or systolic dysfunction;

(ix) prevention and/or treatment of gastrointestinal diseases, such as inflammatory bowel syndrome; small bowel syndrome, or Crohn's disease; dyspepsia; and/or gastric ulcers;

(x) prevention and/or treatment of critical illness, such as treatment of a critically ill patient, a critical illness polynephropathy (CIPNP) patient, and/or a potential CIPNP patient; prevention of critical illness or development of CIPNP; prevention, treatment and/or cure of systemic inflammatory response syndrome (SIRS) in a patient; and/or for the prevention or reduction of the likelihood of a patient suffering from bacteraemia, septicaemia, and/or septic shock during hospitalisation; and/or (xi) prevention and/or treatment of polycystic ovary syndrome (PCOS).

In a particular embodiment, the indication is selected from the group consisting of (i)-(iii) and (v)-(iix), such as indications (i), (ii), and/or (iii); or indication (v), indication (vi), indication (vii), and/or indication (iix).

In another particular embodiment, the indication is (i). In a further particular embodiment the indication is (v). In a still further particular embodiment the indication is (iix).

In some embodiments the invention relates to a composition or a granulate of the invention for treatment of diabetes or obesity, wherein said granulate is administered orally. In some embodiments the invention relates to a method for treatment of diabetes or obesity comprising oral administration of a composition comprising a composition or a granulate of the invention to a patient in need thereof.

The following indications are particularly preferred: Type 2 diabetes, and/or obesity.

EMBODIMENTS OF THE INVENTION

The following are non-limiting examples of embodiments of the invention:
1. A tablet comprising a granulate comprising i) no more than 15% (w/w) peptide, and ii) at least 50% (w/w) salt of NAC, wherein said tablet has
   a) a bulk density of at least 0.90 g/cm³;
   b) a median pore diameter of no more than 1.5 μm; and/or
   c) a maximum pore diameter of no more than 4 μm.
2. A tablet comprising a granulate comprising i) no more than 15% (w/w) peptide, and ii) at least 50% (w/w) salt of NAC, wherein said tablet has
   a) a bulk density of at least 0.90 g/cm³;
   b) a median pore diameter of no more than 1.5 μm;
   c) a maximum pore diameter of no more than 4 μm; and/or
   d) a crushing strength of at least 50 N, such as 50-400 N.
3. A tablet comprising a granulate comprising i) no more than 15% (w/w) peptide, and ii) at least 50% (w/w) salt of NAC, wherein said tablet has
   a) a bulk density, such as a bulk density, of at least 0.90 g/cm³;
   b) a median pore diameter of no more than 1.5 μm;
   c) a maximum pore diameter of no more than 4 μm;
   d) a crushing strength of at least 50 N, such as 50-400 N; and/or
   e) a disintegration time of 12-18 minutes for a tablet with a total weight of 300-500 mg comprising at least 60% (w/w) salt of NAC.

4. A tablet according to any one of the preceding embodiments, wherein said tablet does not contain a disintegrant.
5. A tablet according to any one of the preceding embodiments, wherein said disintegration time is no more than 22 minutes and/or said bulk density is no more than 1.19 g/cm³.
6. A tablet according to any one of the preceding embodiments, wherein said peptide comprises substituent comprising a fatty acid or a fatty diacid, such as formula (X)

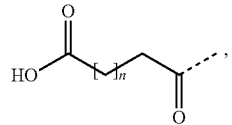

wherein n is at least 13.
7. A tablet according to any one of the preceding embodiments, wherein said peptide comprises one or more 8-amino-3,6-dioxaoctanoic acid (OEG).
8. A tablet according to any one of the preceding embodiments, wherein said peptide is an acylated peptide or a GLP-1 peptide, such as an acylated GLP-1 peptide.
9. A tablet according to any one of the preceding embodiments, wherein said tablet is for oral administration.
10. A tablet according to any one of the preceding embodiments, wherein the amount of peptide is no more than 10% (w/w), such as 1-5% (w/w).
11. A tablet according to any one of the preceding embodiments, wherein the amount of said salt of NAC is 50-90% (w/w), such as 55-85% (w/w) or 70-80% (w/w).
12. A tablet according to any one of the preceding embodiments, wherein said tablet comprises a lubricant, such as magnesium stearate.
13. A tablet according to any one of the preceding embodiments, wherein the amount of said lubricant is no more than 3% (w/w), such as 1.5-3.0% (w/w).
14. A tablet according to any one of the preceding embodiments, wherein said tablet comprises a binder, such as povidone.
15. A tablet according to any one of the preceding embodiments, wherein said granulate comprises a filler, such as microcrystalline cellulose.
16. A tablet according to any one of the preceding embodiments, wherein said tablet comprises a granulate comprising said peptide, said salt of NAC and optionally a binder.
17. A tablet according to any one of the preceding embodiments, wherein said tablet comprises an intragranular and an extragranular part, wherein said extragranular part comprises said lubricant and optionally a filler.
18. A tablet according to any one of the preceding embodiments, wherein said peptide is a GLP-1 peptide, such as semaglutide.
19. A tablet according to any one of the preceding embodiments, wherein said salt of NAC is monosodium NAC (SNAC), such as anhydrous SNAC monosodium salt.
20. A tablet according to any one of the preceding embodiments, wherein said tablet comprises
   a) a granulate comprising
      i) 1-15% (w/w) peptide,
      ii) 55-85% (w/w) salt of NAC, and
      iii) 1-20% (w/w) binder;
   b) 10-35% (w/w) filler; and
   c) 0.5-3% (w/w) lubricant.

21. A tablet according to any one of the preceding embodiments, wherein said tablet comprises
   a) a granulate comprising
      i) 1-100 mg, such as 10 mg, peptide,
      ii) 100-1000 mg, such as 300 mg, salt of NAC, and
      iii) 1-20 mg, such as 8 mg, binder;
   b) 20-200 mg, such as 100 mg, filler; and
   c) 0.5-8 mg, such as 2-8 mg, lubricant.
22. A tablet according to any one of the preceding embodiments, wherein said tablet was prepared by exerting a compression force of at least 5 kN, such as at least 10 kN or at least 15 kN, or no more than 25 kN, such as no more than 20 kN or 5-25 kN.
23. A tablet according to any one of the preceding embodiments, wherein said tablet has a weight of 300-500 mg.
24. A tablet according to any one of the preceding embodiments, wherein said tablet has a bulk density of at least 0.90 g/cm$^3$, such as at least 0.95 g/cm$^3$ or at least 1.0 g/cm$^3$, or such as at least 1.1 g/cm$^3$ or at least 1.2 g/cm$^3$.
25. A tablet according to any one of the preceding embodiments, wherein said tablet has a median pore diameter of no more than 1.5 μm, such as no more than 1.3 μm or no more than 1.0 μm.
26. A tablet according to any one of the preceding embodiments, wherein said tablet has a maximum pore diameter of no more than 4 μm, such as no more than 3.5 μm or no more than 3 μm.
27. A tablet according to any one of the preceding embodiments, wherein said tablet has a crushing strength of at least 50 N, such as at least 100 N.
28. A tablet according to any one of the preceding embodiments, wherein said tablet has a disintegration time of 11-18 minutes, such as 12-18 minutes, 12-17 minutes or 13-15 minutes, and wherein said tablet has a total weight of 300-500 mg and comprises at least 60% (w/w) salt of NAC.
29. A tablet according to any one of the preceding embodiments, wherein said density is determined by Assay (Ia) as described herein.
30. A tablet according to any one of the preceding embodiments, wherein said median pore diameter or maximum pore diameter is determined by Assay (IIb) as described herein.
31. A tablet according to any one of the preceding embodiments, wherein said crushing strength is determined by Assay (III) as described herein.
32. A tablet according to any one of the preceding embodiments, wherein said disintegration time is determined by Assay (IV) as described herein.
33. A tablet as defined in any one of the preceding embodiments for use in medicine.
34. A tablet as defined in any one embodiments 1-32 for treating type 2 diabetes or obesity.
35. A method for treating type 2 diabetes or obesity comprising administering a tablet as defined in any one of embodiments 1-32 to a patient in need thereof.
36. Use of a tablet as defined in any one of embodiments 1-32 for the preparation of a medicament.
37. Use of a tablet as defined in any one of embodiments 1-32 for the preparation of a medicament for treating type 2 diabetes or obesity.
38. A granulate comprising i) no more than 15% (w/w) peptide, and ii) at least 50% (w/w) salt of NAC.
39. A granulate according to embodiment 38, wherein said granulate comprises i) 1-5% (w/w) peptide, ii) 55-85% (w/w) salt of NAC, and iii) 1-20% (w/w) binder.
40. A granulate according to embodiment 38 or 39, wherein said granulate comprises i) 1-100 mg, such as 10 mg, peptide, ii) 100-1000 mg, such as 300 mg, salt of NAC, and iii) 1-20 mg, such as 8 mg, povidone.
41. A granulate according to any one of embodiments 38-40, wherein said granulate is as defined in any one of embodiments 1-32.
42. A process for the preparation of a tablet comprising a granulate comprising i) no more than 15% (w/w) peptide, such as GLP-1 peptide, and ii) at least 50% (w/w) salt of NAC, said process comprising the step of exerting a compression force when punching said tablet of
   a) at least 5 kN, such as 5-25 kN, or
   b) at least 4 kN/cm$^2$.
43. A process according to embodiment 42, wherein said compression force is at least 5 kN, such as 5-25 kN, at least 10 kN or at least 15 kN, or b) at least 4 kN/cm$^2$, such as at least 6 kN/cm$^2$ or at least 8 kN/cm$^2$.
44. A process according to embodiment 42 or 43, wherein said compression force is no more than 25 kN, such as no more than 20 kN.
45. A process according to any one of embodiments 42-44, wherein said process comprises a pre-compression step.
46. A process according to any one of embodiments 42-45, wherein said tablet is as defined in any one of embodiments 1-32.
47. A method for controlling porosity of a group of tablets, said method comprising the steps of:
   a) determining the near-infrared (NIR) spectrum of a selection of tablets;
   b) comparing said spectrum to a reference NIR spectrum, or performing a statistical analysis of said spectrum to determine the tablet porosity; and
   c) selecting a subgroup of tablets with a NIR spectrum or porosity within a predetermined range.
48. A method according to embodiment 47, wherein said method is an at-line NIR method.
49. A method according to embodiment 47, wherein said method is an in-line NIR method.
50. A method according to 49, wherein said method comprises continuous measurement of porosity.
51. A method according to any one of embodiments 47-50, wherein said spectrum is compared to a reference spectrum.
52. A method according to any one of embodiments 47-51, wherein tabletting parameters are adjusted during tabletting in order to improve the porosity of the tablets.
53. An method according to any one of embodiments 47-52, wherein a subgroup of tablets with the desired porosity is obtained.
54. A method according to any one of embodiments 47-53, wherein said tablet is as defined in any one of embodiments 1-32.

FURTHER EMBODIMENTS OF THE INVENTION

The following are further non-limiting examples of embodiments of the invention:
1. A tablet comprising a granulate comprising i) no more than 15% (w/w) peptide, and ii) at least 50% (w/w) salt of NAC, wherein said tablet has
   a) a bulk density of at least 0.90 g/cm$^3$;
   b) a median pore diameter of no more than 1.5 μm; and/or
   c) a maximum pore diameter of no more than 4 μm.
2. A tablet comprising a granulate comprising i) no more than 15% (w/w) peptide, and ii) at least 50% (w/w) salt of NAC, wherein said tablet has
   a) a bulk density of at least 0.90 g/cm$^3$;
   b) a median pore diameter of no more than 1.5 μm;

c) a maximum pore diameter of no more than 4 µm; and/or
d) a crushing strength of at least 50 N, such as 50-400 N.

3. A tablet comprising a granulate comprising i) no more than 15% (w/w) peptide, and ii) at least 50% (w/w) salt of NAC, wherein said tablet has
   a) a bulk density, such as a bulk density, of at least 0.90 g/cm³;
   b) a median pore diameter of no more than 1.5 µm;
   c) a maximum pore diameter of no more than 4 µm;
   d) a crushing strength of at least 50 N, such as 50-400 N; and/or
   e) a disintegration time of 12-18 minutes for a tablet with a total weight of 300-500 mg comprising at least 60% (w/w) salt of NAC.

4. A tablet comprising a granulate comprising i) no more than 15% (w/w) peptide, and ii) at least 60% (w/w) salt of NAC, wherein said tablet has
   a) a bulk density, such as a bulk density, of at least 0.90 g/cm³;
   b) a median pore diameter of no more than 1.5 µm;
   c) a maximum pore diameter of no more than 4 µm;
   d) a crushing strength of at least 50 N, such as 50-400 N; and/or
   e) a disintegration time of 12-18 minutes for a tablet with a total weight of 300-500 mg comprising at least 60% (w/w) salt of NAC.

5. A tablet comprising a granulate comprising i) no more than 15% (w/w) peptide, and ii) at least 50% (w/w) salt of NAC, which has a bulk density of at least 0.90 g/cm³; wherein said tablet further has
   a) a median pore diameter of no more than 1.5 µm; and/or
   b) a maximum pore diameter of no more than 4 µm.

6. A tablet comprising a granulate comprising i) no more than 15% (w/w) peptide, and ii) at least 50% (w/w) salt of NAC, which has a bulk density of at least 0.90 g/cm³; wherein said tablet further has
   a) a median pore diameter of no more than 1.5 µm;
   b) a maximum pore diameter of no more than 4 µm; and/or
   c) a crushing strength of at least 50 N, such as 50-400 N.

7. A tablet comprising a granulate comprising i) no more than 15% (w/w) peptide, and ii) at least 50% (w/w) salt of NAC, which has a bulk density of at least 0.90 g/cm³; wherein said tablet further has
   a) a median pore diameter of no more than 1.5 µm;
   b) a maximum pore diameter of no more than 4 µm; and/or
   c) a crushing strength of at least 50 N, such as 50-400 N; and/or
   d) a disintegration time of 12-18 minutes for said tablet with a total weight of 300-500 mg.

8. A tablet according to any one of the preceding embodiments which is surface eroding.

9. A tablet according to any one of the preceding embodiments, wherein said tablet does not contain a superdisintegrant.

10. A tablet according to any one of the preceding embodiments, wherein said tablet does not contain sodium starch glycolate, sodium carboxymethyl starch, crospovidone or croscarmellose sodium.

11. A tablet according to any one of the preceding embodiments, wherein the tablet is dry granulated.

12. A tablet according to any one of the preceding embodiments, wherein said disintegration time is no more than 22 minutes and/or said bulk density is no more than 1.19 g/cm³.

13. A tablet according to any one of the preceding embodiments, wherein said peptide comprises substituent comprising a fatty acid or a fatty diacid, such as formula (X)

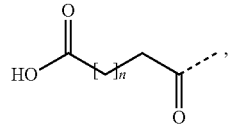

wherein n is at least 13.

14. A tablet according to any one of the preceding embodiments, wherein said peptide comprises one or more 8-amino-3,6-dioxaoctanoic acid (OEG).

15. A tablet according to any one of the preceding embodiments, wherein said peptide is an acylated peptide or a GLP-1 peptide, such as an acylated GLP-1 peptide.

16. A tablet according to any one of the preceding embodiments, wherein said tablet is for oral administration.

17. A tablet according to any one of the preceding embodiments, wherein the amount of peptide is no more than 10% (w/w), such as 1-5% (w/w).

18. A tablet according to any one of the preceding embodiments, wherein the amount of said salt of NAC is 50-90% (w/w), such as 55-85% (w/w) or 70-80% (w/w).

19. A tablet according to any one of the preceding embodiments, wherein said tablet comprises a lubricant, such as magnesium stearate.

20. A tablet according to any one of the preceding embodiments, wherein the amount of said lubricant is no more than 3% (w/w), such as 1.5-3.0% (w/w).

21. A tablet according to any one of the preceding embodiments, wherein said tablet comprises a binder, such as povidone.

22. A tablet according to any one of the preceding embodiments, wherein said granulate comprises a filler, such as microcrystalline cellulose.

23. A tablet according to any one of the preceding embodiments, wherein said tablet comprises a granulate comprising said peptide, said salt of NAC and optionally a binder.

24. A tablet according to any one of the preceding embodiments, wherein said tablet comprises an intragranular and an extragranular part, wherein said extragranular part comprises said lubricant and optionally a filler.

25. A tablet according to any one of the preceding embodiments, wherein said peptide is a GLP-1 peptide.

26. A tablet according to any one of the preceding embodiments, wherein said peptide is N-epsilon26-[2-(2-{2-[2-(2-{2-[(S)-4-carboxy-4-(17-carboxyheptadecanoylamino)butyrylamino]-ethoxy}ethoxy)acetylamino]ethoxy}ethoxy)acetyl][Aib8,Arg34]GLP-1(7-37).

27. A tablet according to any one of the preceding embodiments, wherein said salt of NAC is monosodium NAC (SNAC), such as anhydrous SNAC monosodium salt.

28. A tablet according to any one of the preceding embodiments, wherein said tablet comprises
   a) a granulate comprising
      i) 1-15% (w/w) peptide,
      ii) 55-85% (w/w) salt of NAC, and
      iii) 1-20% (w/w) binder;
   b) 10-35% (w/w) filler; and
   c) 0.5-3% (w/w) lubricant.

29. A tablet according to any one of the preceding embodiments, wherein said tablet comprises
   a) a granulate comprising
      i) 1-100 mg, such as 10 mg, peptide,
      ii) 100-1000 mg, such as 300 mg, salt of NAC, and
      iii) 1-20 mg, such as 8 mg, binder;
   b) 20-200 mg, such as 100 mg, filler; and
   c) 0.5-8 mg, such as 2-8 mg, lubricant.
30. A tablet according to any one of the preceding embodiments, wherein said tablet was prepared by exerting a compression force of at least 5 kN, such as at least 10 kN or at least 15 kN, or no more than 25 kN, such as no more than 20 kN or 5-25 kN.
31. A tablet according to any one of the preceding embodiments, wherein said tablet has a weight of 300-500 mg.
32. A tablet according to any one of the preceding embodiments, wherein said tablet has a weight of 300-400 mg.
33. A tablet according to any one of the preceding embodiments, wherein said tablet has a weight of about 300 mg.
34. A tablet according to any one of the preceding embodiments, wherein said tablet has a weight of about 400 mg.
35. A tablet according to any one of the preceding embodiments, wherein said tablet has a weight of about 430 mg, such as 427 mg.
36. A tablet according to any one of the preceding embodiments, wherein said tablet has a bulk density of at least 0.90 g/cm$^3$, such as at least 0.95 g/cm$^3$ or at least 1.0 g/cm$^3$, or such as at least 1.1 g/cm$^3$ or at least 1.2 g/cm$^3$.
37. A tablet according to any one of the preceding embodiments, wherein said tablet has a bulk density of no more than 1.2 g/cm$^3$, such as no more than 1.19 g/cm$^3$.
38. A tablet according to any one of the preceding embodiments, wherein said tablet has a bulk density of about 1.2 g/cm$^3$, such as about 1.15 g/cm$^3$.
39. A tablet according to any one of the preceding embodiments, wherein said tablet has a median pore diameter of no more than 1.5 μm, such as no more than 1.3 μm or no more than 1.0 μm.
40. A tablet according to any one of the preceding embodiments, wherein said tablet has a median pore diameter of about 92 nm.
41. A tablet according to any one of the preceding embodiments, wherein said tablet has a maximum pore diameter of no more than 4 μm, such as no more than 3.5 μm or no more than 3 μm.
42. A tablet according to any one of the preceding embodiments, wherein said tablet has a maximum pore diameter of no more than 2.5 μm, such as no more than 2 μm, no more than 1.5 μm, or no more than 1 μm.
43. A tablet according to any one of the preceding embodiments, wherein said tablet has a maximum pore diameter of about 0.1 μm.
44. A tablet according to any one of the preceding embodiments, wherein said tablet has a crushing strength of at least 50 N, such as at least 100 N.
45. A tablet according to any one of the preceding embodiments, wherein said tablet has a crushing strength of no more than 400 N.
46. A tablet according to any one of the preceding embodiments, wherein said tablet has a crushing strength of about 120 N.
47. A tablet according to any one of the preceding embodiments, wherein said tablet has a disintegration time of 10-18 minutes, such as 10-17 minutes or 10-13 minutes, and wherein said tablet has a total weight of 300-500 mg and comprises at least 60% (w/w) salt of NAC.
48. A tablet according to any one of the preceding embodiments, wherein said tablet has a disintegration time of 11-18 minutes, such as 12-18 minutes, 12-17 minutes or 13-15 minutes, and wherein said tablet has a total weight of 300-500 mg and comprises at least 60% (w/w) salt of NAC.
49. A tablet according to any one of the preceding embodiments, wherein said tablet has a disintegration time of 9-11 minutes for a tablet with a total weight of 300-500 mg and comprises at least 60% (w/w) salt of NAC.
50. A tablet according to any one of the preceding embodiments, which causes gradual release of said salt of NAC in vivo.
51. A tablet according to any one of the preceding embodiments, wherein Cmax in plasma of said salt of NAC is less than 900 ng/ml upon oral administration of said tablet.
52. A tablet according to any one of the preceding embodiments comprising approximately 1 mmol salt of NAC, wherein Cmax in plasma of said salt of NAC is less than 900 ng/ml upon oral administration of said tablet.
53. A tablet according to any one of the preceding embodiments, wherein said density is determined by Assay (Ia) as described herein.
54. A tablet according to any one of the preceding embodiments, wherein said median pore diameter or maximum pore diameter is determined by Assay (IIb) as described herein.
55. A tablet according to any one of the preceding embodiments, wherein said crushing strength is determined by Assay (III) as described herein.
56. A tablet according to any one of the preceding embodiments, wherein said disintegration time is determined by Assay (IV) as described herein.
57. A tablet comprising a granulate comprising i) about 5% (w/w) N-epsilon26-[2-(2-{2-[2-(2-{2-[(S)-4-carboxy-4-(17-carboxyheptadecanoylamino)butyrylamino]ethoxy}ethoxy)-acetylamino]ethoxy}ethoxy)acetyl][Aib8, Arg34]GLP-1(7-37), and ii) about 70% (w/w) salt of NAC, wherein said tablet has
   a) a bulk density of about 1.15 g/cm$^3$;
   b) a median pore diameter of about 92 nm;
   c) a maximum pore diameter of about 0.1 μm;
   d) a crushing strength of about 120 N; and
   e) a disintegration time of 9-11 minutes for a tablet with a total weight of about 430 mg, such as 427 mg.
58. A tablet as defined in any one of the preceding embodiments for use in medicine.
59. A tablet as defined in any one of embodiments 1-57 for treating type 2 diabetes or obesity.
60. A method for treating type 2 diabetes or obesity comprising administering a tablet as defined in any one of embodiments 1-57 to a patient in need thereof.
61. Use of a tablet as defined in any one of embodiments 1-57 for the preparation of a medicament.
62. Use of a tablet as defined in any one of embodiments 1-57 for the preparation of a medicament for treating type 2 diabetes or obesity.
63. A granulate comprising i) no more than 15% (w/w) peptide, and ii) at least 50% (w/w) salt of NAC.
64. A granulate according to embodiment 63, wherein said granulate comprises i) 1-5% (w/w) peptide, ii) 55-85% (w/w) salt of NAC, and iii) 1-20% (w/w) binder.
65. A granulate according to embodiment 63 or 64, wherein said granulate comprises i) 1-100 mg, such as 10 mg, peptide, ii) 100-1000 mg, such as 300 mg, salt of NAC, and iii) 1-20 mg, such as 8 mg, povidone.
66. A granulate according to any one of embodiments 63-65, wherein said granulate is as defined in any one of embodiments 1-57.

67. A granulate according to any one of embodiments 63-65 for use in a tablet according to any one of embodiments 1-57.

68. A process for the preparation of a tablet comprising a granulate comprising i) no more than 15% (w/w) peptide, such as GLP-1 peptide, and ii) at least 50% (w/w) salt of NAC, said process comprising the step of exerting a compression force when punching said tablet of
   a) at least 5 kN, such as 5-25 kN, or
   b) at least 4 kN/cm².

69. A process according to embodiment 68, wherein said compression force is at least 5 kN, such as 5-25 kN, at least 10 kN or at least 15 kN, or b) at least 4 kN/cm², such as at least 6 kN/cm² or at least 8 kN/cm².

70. A process according to embodiment 68 or 69, wherein said compression force is no more than 25 kN, such as no more than 20 kN.

71. A process according to any one of embodiments 68-70, wherein said process comprises a pre-compression step.

72. A process according to any one of embodiments 68-71, wherein said tablet is as defined in any one of embodiments 1-57.

73. A method for controlling porosity of a group of tablets, said method comprising the steps of:
   a) determining the near-infrared (NIR) spectrum of a selection of tablets;
   b) comparing said spectrum to a reference NIR spectrum, or performing a statistical analysis of said spectrum to determine the tablet porosity; and
   c) selecting a subgroup of tablets with a NIR spectrum or porosity within a predetermined range.

74. A method according to embodiment 73, wherein said method is an at-line NIR method.

75. A method according to embodiment 73, wherein said method is an in-line NIR method.

76. A method according to 75, wherein said method comprises continuous measurement of porosity.

77. A method according to any one of embodiments 73-76, wherein said spectrum is compared to a reference spectrum.

78. A method according to any one of embodiments 73-77, wherein tabletting parameters are adjusted during tabletting in order to improve the porosity of the tablets.

79. A method according to any one of embodiments 73-78 having a further step between step b) and c), wherein tablet compression force is adjusted based on results from step b) to obtain a group of tables with the desired porosity.

80. A method according to embodiment 79, wherein tablet compression force in said further step between step b) and c) is reduced if results from step b) show that porosity of the tablets is lower than desired, or increased if results from step b) show that porosity of the tablets is higher than desired.

81. A method according to any one of embodiments 73-78, wherein a subgroup of tablets with the desired porosity is obtained.

82. A method according to any one of embodiments 73-81, wherein said tablet is as defined in any one of embodiments 1-57.

EXAMPLES

Materials and Methods

The GLP-1 compound semaglutide may be prepared using the method described in WO2006/097537, Example 4.

The delivery agent SNAC may be prepared using the method described in WO00/046182 or WO2008/028859.

General Methods of Preparation

The manufacturing process of tablets comprised of 3 major unit processes, i.e. granulation, blending and compression. The manufacturing process additionally comprised a number of secondary unit operations such as dry-sieving of granulate and sieving of excipients, which may be carried out according to common general knowledge of a skilled person.

Wet Granulation

For a batch size of 160 tablets (48 g SNAC) typically 13.8 ml water was used for wet granulation. Approximately 80% (w/w) of the total amount of water was filled into a vial and peptide (e.g. GLP-1) was added. The vial was placed on a Boule mixer, which gently tumbled the vial until all the material was dissolved. Then pH was adjusted to 8.5 with 1-2 N NaOH solution or 0.2 N HCl solution. Finally, water was added in order to obtain 100% of the total amount of water.

SNAC and Povidone were blended in a high-shear mixer, such as Diosna high-shear mixer or Rowenta mixer, for 1-3 minutes. Then the granulation solution with dissolved peptide (e.g. GLP-1) was added with a uniform rate over 1-2 minutes using a pipette or syringe. Purified water was added if more granulation fluid was needed. The wet granulation was stopped 10-15 seconds after addition of the granulation solution. The granulate was dried in an oven for minimum 16 hours at 45° C. to a moisture content lower than 2.5% as determined by Karl Fisher titration or loss on drying. The dried granulate was passed through a 0.5 mm sieve.

This method is also referred to as "wet" herein.

Dry Granulation—Method A

Dry granulation was performed by roller compaction of a blend of SNAC, semaglutide, povidone, microcrystalline cellulose and magnesium stearate on a Gerteis Micro-Pactor®. Ribbons were milled with a KitchenAid mill and sieved through a 500 μm mesh. The granulated powder was further blended with extragranular magnesium stearate (2.3 mg per tablet) for 3 minutes on a Turbula mixer before compression into tablets.

This method is also referred to as "dry A" herein.

Dry Granulation—Method B

A blend of SNAC and magnesium stearate in the mass ratio 195:5 (SNAC:magnesium stearate) was dry granulated. The remaining magnesium stearate was added extragranularly during blending subsequent to dry granulation. Dry granulation was carried out by roller compaction on a Gerteis MINI-PACTOR using smooth rolls, a 0.63 mm wire mesh screen, and a granulator speed of 60 rpm. The roll speed was set at 1.5 or 3.0 rpm and roller compaction forces around 1 to 13 kN/cm were applied at a gap of 1.0 mm. Subsequent to dry granulation comminution of the moldings into granules was carried out.

This method is also referred to as "dry B" herein.

Blending

The granules were blended with extragranular excipients (e.g. filler and lubricant) in several sub-steps before compression. Blending was first done with microcrystalline cellulose for 8-10 minutes and then with extragranular magnesium stearate for 3 minutes on a Turbula mixer at 32 rpm in an equal volume to volume manner.

Compression

The powder blend was compressed into tablets on e.g. a Fette 102i rotary tablet press, a Korsch PH 100 tablet press, or a DIAF single punch press. An optional pre-compression step was applied before the main compression to reduce the amount of entrapped air during the main compression.

General Methods of Detection and Characterisation

Assay (I): Density

The tablet volume and weight was measured. From these measures, the bulk density could be calculated as the mass of the tablet divided by the volume.

Assay (IIa): Calculated Porosity

The tablet volume and weight was measured. From these measures, the bulk density could be calculated as the mass of the tablet divided by the volume. Assuming a skeletal density of the tablet of 1.38 g/cm³ the solid fraction could be calculated as tablet bulk density divided by tablet skeletal density. The porosity is then 1 minus the solid fraction.

Assay (IIb): Mercury Porosimetry

The porosity analysis utilized a Micromeritics Autopore IV model 9520 with Autopore IV 9500 software version 1.06. The sample amount was adjusted in order to use 10-90% of the stem volume. The sample was evacuated to 50 μmHg for 5 minutes. The sample cell was then filled with mercury at a filling pressure of 0.0032 MPa, Mercury intrusion was performed in the pressure range from 0.0007 to 420 MPa Assay (III): Crushing Strength The crushing strength of the tablets was measured with a Pharma Test apparatus (33AA02). The test measures the force required to disrupt the tablet, and the test was based on the pharmacopeia method Ph Eur 2.9.8.

Assay (IV): Disintegration Test

The disintegration test was carried out using a Pharma Test PTZ AUTO disintegration test apparatus. The setup is based on pharmacopeia method Ph Eur 2.09.01, Test A (Basket-rack assembly). The disintegration apparatus consists of a basket rack holding 2×6 plastic tubes, open at the top and bottom, the bottom of the tube is covered by a screen. SNAC tablets are placed in the tubes and on top of the tablets are placed discs for automated disintegration detection. The basket is immersed in 800 ml purified water held at 37° C., in a 1 L beaker. Time for complete disintegration was measured. Furthermore, tablets were observed visually for surface eroding behaviour during the disintegration test.

Assay (V): Dissolution Test

The dissolution test was conducted with apparatus 2 in accordance with United States Pharmacopoeia 35 using a paddle rotation speed of 50 rpm. The 500 mL dissolution medium of phosphate buffer (pH 6.8) was used at a temperature of 37° C. The dissolution media had a content of 0.1% Tween80. Sample aliquots were removed at appropriate intervals. Release was determined using a RP-HPLC method for dual detection of SNAC and semaglutide. The content was calculated based on the peak area of the SNAC and semaglutide peaks in the chromatogram relative to the peak areas of the SNAC and semaglutide references, respectively. The HPLC method was based on gradient elution on a C8 column. The solvent system was trifluoroacetic acid and acetonitrile with UV detection at 210 nm.

Assay (VI): Oral Administration to Beagle Dogs

Animals, Dosing and Blood Sampling:

Beagle dogs, weighing 6-17 kg during the study period were included in the study. The dogs were dosed in fasting state. The compositions were administered by a single oral dosing to the dogs in groups of 8 dogs. Blood samples were taken at the following time points: predose, 0.25, 0.5, 0.75, 1, 1.5, 2, 2.5, 3, 4, 6, 8, 24, 48, 72, 96, 120, 144, 192 and 240 hours post dosing. The i.v. solution (20 nmol/mL in a pH 7.4 solution comprising 0.1 mg/ml Tween 20, 5.5 mg/ml Phenol, 1.42 mg/ml Na2HPO4 and 14 mg/ml Propylene Glycol) was dosed in a dose volume of 0.1 mL/kg in the same dog colony in one dosing group (n=8). Blood samples were taken at the following time points: predose, 0.25, 0.5, 0.75, 1, 1.5, 2, 2.5, 3, 4, 6, 8, 24, 48, 72, 96, 120, 144, 192 and 240 hours post dosing.

Preparation of Plasma:

All blood samples were collected into test tubes containing EDTA for stabilisation and kept on ice until centrifugation. Plasma was separated from whole blood by centrifugation and the plasma was stored at −20° C. or lower until analysis.

Analysis of Plasma Samples:

The plasma was analysed for semaglutide using a Luminescence Oxygen Channeling Immunoassay (LOCI). The LOCI assay employs donor beads coated with streptavidin and acceptor beads conjugated with a monoclonal antibody binding to a mid-molecular region of semaglutide. The other monoclonal antibody, specific for an N-terminal epitope, was biotinylated. In the assay the three reactants were combined with the semaglutide which form a two-sited immuno-complex. Illumination of the complex releases singlet oxygen atoms from the donor beads which channels into the acceptor beads and trigger chemiluminescence which was measured in the EnVision plate reader. The amount of light was proportional to the concentration of semaglutide and the lower limit of quantification (LLOQ) in plasma was 100 μM.

Example 1: Preparation of Tablets

Tablets comprising GLP-1 and SNAC with compositions as described in Table 1 were prepared by granulation, blending, and compression as described in the section General Methods of Preparation, wherein during compression of composition A the compression force was varied to obtain tablets with varying disintegration times by adjusting the height of the tablets;

tablets from composition D were prepared by direct compression of a granulate formed by dry granulation by exerting a compression force of 5.2, 10.2, 14.9, 20.9, or 25.9 kN; and for tablets from composition E a pre-compression step was applied setting the tablet band height to 3.5 mm, tablets were prepared by exerting a compression force of 4.0, 5.5, 7.0, or 10.5 kN, and the tablet band height of the final tablets was set between 1.24 and 1.89 mm.

TABLE 1

Composition of tablets (amounts are expressed as "per tablet")

| Composition | A | B | C | D | E | F |
|---|---|---|---|---|---|---|
| Semaglutide (mg) | 10 | 10 | 20 | 10 | 10 | 10 |
| SNAC (mg) | 300 | 300 | 600 | 300 | 300 | 300 |
| Povidone K 90 (mg) | 8-16 | 8 | 16 | 8 | 8 | 8 |
| Microcrystalline cellulose (mg) | 78-156 | 78 | 156 | 100 | 100 | 78 |

TABLE 1-continued

Composition of tablets (amounts are expressed as "per tablet")

| Composition | A | B | C | D | E | F |
|---|---|---|---|---|---|---|
| Magnesium Stearate (mg) | 4 | 4 | 8 | 7.7 (intragr.) 2.3 (extragr.) | 7.7 (intragr.) 1.6 (extragr.) | 7.7 (intragr.) 2.0 (extragr.) |
| Sodium polystyrene sulfonate resin with 1 MBq 111Indium chloride | na | na | na | na | na | 1-20 mg |
| Tablet weight (mg) | 400-498 | 400 | 800 | 428 | 427 | 408.7-427.7 |
| Granulation type (wet, dry A, or dry B) | wet | wet | wet | dry A | dry B | dry B |
| Tablet tooling (mm) Tablet shape | 10 round, deep convex | 13 × 7.5 oval, convex | 18.9 × 10 oval, convex | 10 round, flat | 8.5 × 16 oval, convex | 7.5 × 13 oval, convex |
| Tablet press | DIAF | Korsch PH 100 | Korsch PH 100 | Fette | Fette | Carver model C |
| Pre-compression | no | no | no | no | yes | no |

Example 2: Effect on Tablet Disintegration Time on Oral Bioavailability of Semaglutide in Beagle Dogs Tablets with various crushing strengths and disintegration times were prepared from composition A as described in Example 1 and with an amount of microcrystalline cellulose and povidone as shown in Table 2. Oral bioavailability and absorption kinetics of GLP-1 after administration of the tablets to beagle dogs were determined according to Assay (VI) as described herein. The bulk density was estimated according to Assay (Ia) as described herein. The results are shown in Table 2.

TABLE 2

Oral bioavailability and absorption kinetics of semaglutide after administration of tablets of composition A with various disintegration times to beagle dogs.

| Content of microcrystalline cellulose (mg) | Content of povidone (mg) | Disintegration time (min:sec) | Total tablet weight (mg) | Oral bioavailability (%) | Tmax (hours) | Estimated bulk density (g/cm³) |
|---|---|---|---|---|---|---|
| 78 | 8 | 11:30 | 416 | 0.5 | 0.8 | 1.02 |
| 78 | 8 | 13:25 | 404 | 1.3 | 1.5 | 1.16 |
| 78 | 8 | 14:12 | 415 | 2.4 | 1.2 | 1.17 |
| 120 | 8 | 16:34 | 445 | 1.0 | 1.6 | 1.16 |
| 156 | 16 | 19:14 | 498 | 0.2 | 1.1 | 1.00 |
| 156 | 16 | 23:25 | 497 | 0.3 | 1.7 | 1.20 |

The results demonstrate that 10 mm round tablets with a deep convex face and a total weight of 404-445 mg with a disintegration time of 13-17 minutes are to be preferred, however, this is expected only to apply for tablets of similar composition and weight, i.e. tablets with a total weight of 300-500 mg comprising at least 60% (w/w) salt of NAC.

The results further demonstrate that Tmax for plasma semaglutide was minimum 1 hour for the best performing tablets in contrast to published studies with SNAC and human GLP-1 showing a Tmax of 20-30 minutes. Hence, a somewhat more protracted release of SNAC is desired for peptides with longer oral absorption half-lives, such as acylated GLP-1 peptides.

FIG. 1 shows tablet A before (right), after 5 minutes (middle) and after 10 minutes (left) in a disintegration test according to Assay (IV) as described herein on tablets from the batch having an oral availability of 2.4% in Table 2. The results show that Tablet A has surface eroding properties.

Example 3: Porosity Measurements on Good and Poor Performing Tablets

Tablets were prepared from compositions B, C and E (hereafter referred to as Tablet batch B, Tablet batch C and Tablet batch D, respectively) as described in Example 1 and subjected to mercury porosimetry according to Assay (IIb) as described herein. Tablet batch E (comprising 10 mg semaglutide and 300 mg SNAC) gave the best result in a clinical trial, tablet batch B gave intermediate results, while Tablet batch C (comprising the 20 mg semaglutide and 600 mg SNAC) gave poor results with respect to oral bioavailability. The results are shown in Table 3 and FIG. 2.

TABLE 3

Porosimetry results from mercury intrusion into Tablet batch B, C and E

| | Tablet batch B | Tablet batch C | Tablet batch E |
|---|---|---|---|
| Total Intrusion Volume (mL/g) | 0.27 | 0.41 | 0.15 |
| Total Pore Area (m²/g) | 29.5 | 24.5 | 31.6 |
| Median Pore Diameter (Volume) (μm) | 0.84 | 2.06 | 0.09 |
| Bulk Density at 0.1000 MPa (g/cm³) | 1.00 | 0.88 | 1.15 |
| Apparent (skeletal) Density (g/cm³) | 1.37 | 1.38 | 1.38 |
| Porosity (%) | 27.1 | 36.5 | 17.4 |

Figure 2:
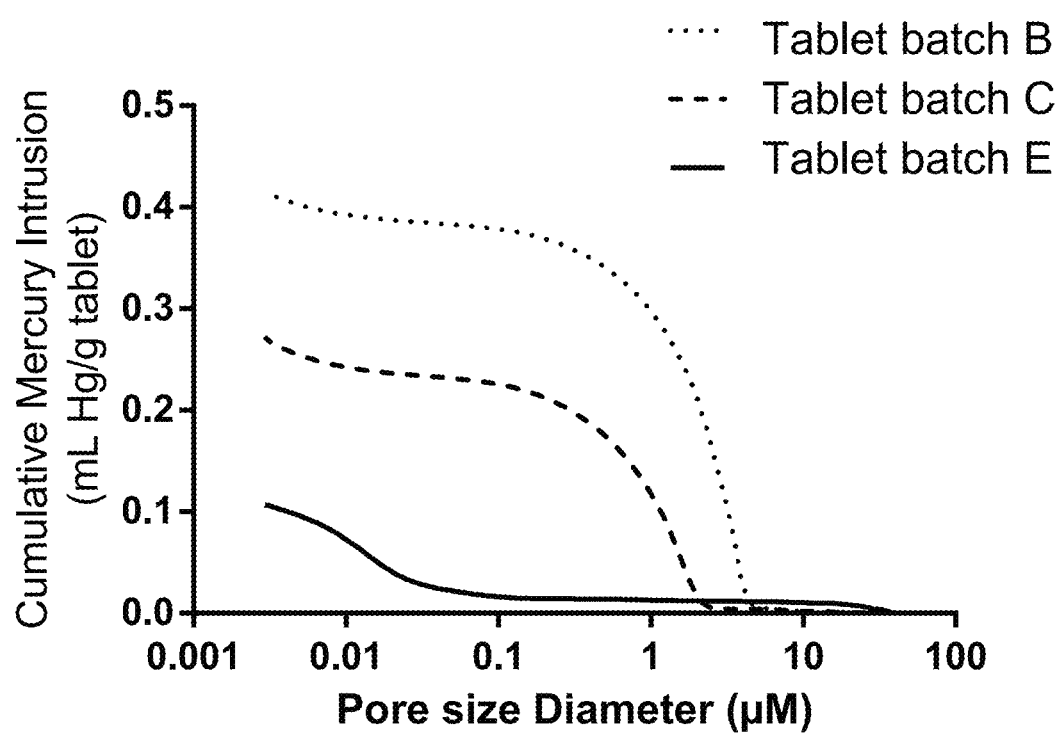
FIG. 2 shows mercury intrusion into Tablet B (dotted line), Tablet C (broken line) and tablet E (solid line) (poor, medium and good performing tablets, respectively).

FIG. 2 shows cumulative mercury intrusion into Tablet batch B, C and E depending on pore diameter. FIG. 2 shows that Tablet batch B has a maximum pore diameter of 2.5 μm whereas Tablet batch C has a maximum pore diameter of 5 µm. FIG. 2 shows a sharp increase in liquid mercury intrusion volume at a pore diameter of 5 µm for Tablet batch C and a more gradual increase of mercury intrusion at a pore diameter of 2.5 µm for Tablet batch B, whereas Tablet batch E prepared by a dry granulation technique showed low amount of pores above 0.1 µm. This shows that especially larger pores are reduced as compression pressure increases, whereas the smaller pores remain intact. Furthermore, dry granulation provides tablets with very low pore size and porosity.

These results show that preferred tablets providing an improved bioavailability can be identified by having a porosity of less than 36.5%, a bulk density larger than 0.90 g/cm$^3$, a median pore diameter less than 2 µm, and/or a maximum pore diameter less than 5 µm.

Example 4: Compactability of Granulate without a Pre-Compression Step

Tablets were prepared from composition D (round and flat faced tablets with a diameter of 10 mm) as described in Example 1. The density, porosity, and crushing strength was determined according to Assay (Ia), (IIa), and (III) as described herein, respectively. The results are shown in Table 4.

TABLE 4

Compression profile and resulting tablet properties

| Compression pressure (kN) | Compression pressure/cm$^2$ (kN) | Crushing strength (N) | Tablet bulk density (g/cm$^3$) | Porosity (1-solid fraction) |
|---|---|---|---|---|
| 5.2 | 6.6 | 73 | 1.02 | 0.26 |
| 10.2 | 13.0 | 156 | 1.16 | 0.16 |
| 14.9 | 19.0 | 197 | 1.22 | 0.12 |
| 20.9 | 26.6 | 221 | 1.25 | 0.09 |
| 25.9 | 33.0 | 234 | 1.27 | 0.08 |

These results show that the compression pressure should be higher than 5.2 kN or the compression pressure per area should be higher than 6.6 kN/cm$^2$ in order to obtain tablets with a density above 1.0 g/cm$^3$ and a porosity of no more than 26%.

Example 5: Compactability of a Granulate with a Pre-Compression Step

Tablets were prepared from composition E (16 mm×8.5 mm oval tablets with a convex face) as described in Example 1. Determination of density, porosity, crushing strength, and disintegration time was carried according to Assay (Ia), (IIa), (III), and (IV) as described herein, respectively. The results are shown in Table 5.

The results show that SNAC tablets with low porosity (<37%) and high density (>1.0 g/cm$^3$) can be prepared at a compression pressure>4.0 kN or at a compression pressure per area of more than 3.8 kN/cm$^2$ when a pre-compression step is included in the tabletting step.

Example 6: Control of Tablet Porosity by Near-Infrared (NIR) Reflectance Spectroscopy NIR reflectance has been demonstrated to be a fast and precise method to control the porosity of tablets comprising SNAC and Semaglutide. Tablets with varying porosity were manufactured by varying the compression force as described in Example 4. A NIR reflectance spectrum was acquired from a group of tablets from each of the applied compressions forces by scanning twice on each side with a Bruker MPA 01 Multi Purpose FT-NIR Analyzer. Subsequently, the spectrum was compared to the porosity value for the tablet, which was determined as described in Example 4, using projections to latent structures (PLS) regression.

Figure 3:
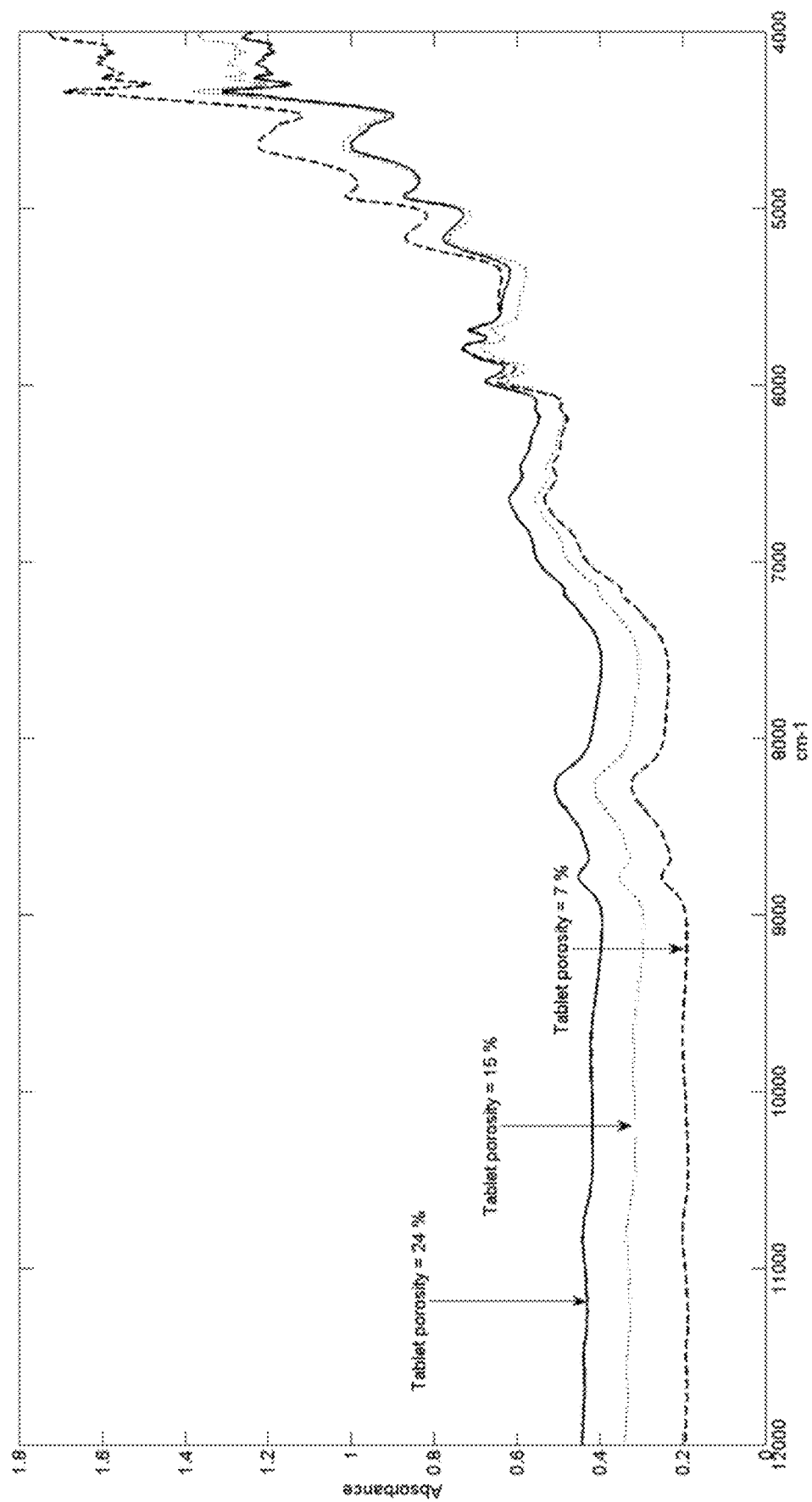
FIG. 3 shows NIR reflectance spectra of three tablets comprising SNAC and Semaglutide with different porosities: 24% (solid line), 15% (dotted line) and 7% (broken line).

FIG. 3 shows the NIR reflectance spectrum of three tablets with porosity of 24%, 15% and 7%. At wavelengths from 12.000 cm$^{-1}$ to 6.000 cm$^{-1}$ is the spectral absorbance increasing with increasing porosity. At wavelengths from 5.000 cm$^{-1}$ to 4.000 cm$^{-1}$ is the spectral absorbance decreasing with increasing porosity.

Figure 4:
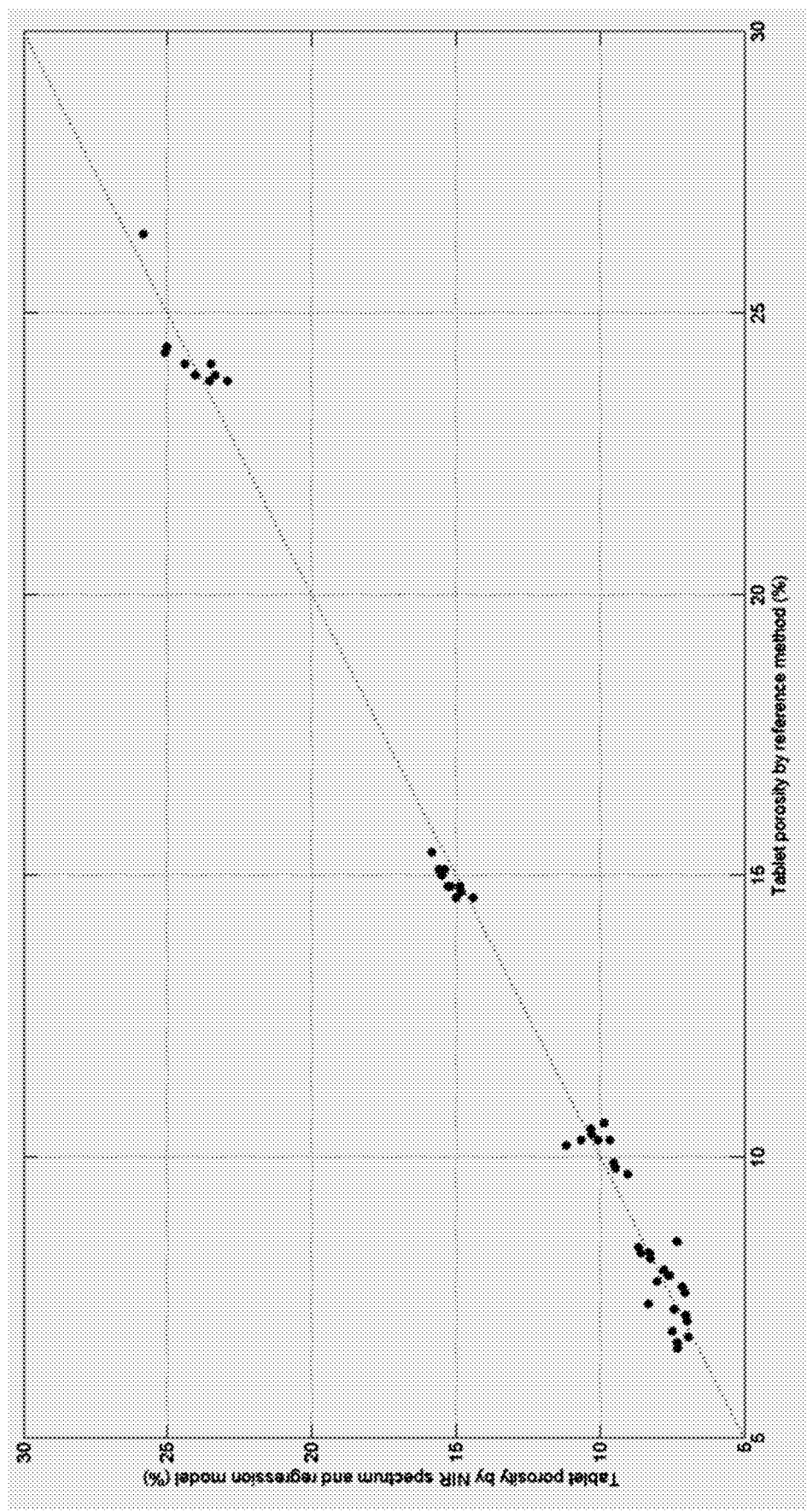
FIG. 4 shows correlation between measured tablet porosity and tablet porosity predicted by NIR spectroscopy.

A statistical regression model was established between the spectra of fifty tablets comprising SNAC and Semaglutide and their corresponding porosity values. With such a regression model is it possible to predict the porosity of future tablet samples based on their NIR reflectance spectrum. The results are shown in FIG. 4 where tablet porosity values (x-axis) for the fifty tablets comprising SNAC and Semaglutide were compared to the tablet porosity predicted by the regression model (y-axis) based on the NIR reflectance spectrum. There was found to be a high correlation between the two methods (R$^2$=0.99).

Accordingly, this method provides a fast and easy determination of tablet porosity on individual tablets with NIR spectroscopy during tabletting. This allows NIR spectroscopy to be used for in-line monitoring of porosity of individual tablets and for adjustment of the tabletting process to achieve tablets with a highly specific porosity.

Furthermore, based on these results it is possible to interface NIR technology with the tabletting machine in three distinct ways and thereby enable real-time control of tablet porosity during tabletting (Table 6).

TABLE 5

Compression profile and resulting tablet properties

| Compression pressure (kN) | Compression pressure/cm$^2$ (kN) | Crushing strength (N) | Disintegration time (min:sec) | Tablet bulk density (g/cm$^3$) | Porosity (fraction) |
|---|---|---|---|---|---|
| 4.0 | 3.8 | 48 | 9:20 | 1.08 | 0.22 |
| 5.5 | 5.2 | 75 | 11:30 | 1.21 | 0.12 |
| 7.0 | 6.6 | 95 | 12:00 | 1.20 | 0.13 |
| 10.5 | 9.9 | 135 | 12:30 | 1.30 | 0.06 |

TABLE 6

Interface opportunity.

| Interface opportunity | Instrumentation | Control |
|---|---|---|
| At-line, full spectrum | Off-the shelf NIR spectrometer. Analysis time ~10-20 seconds/tablet plus sample removal and time for manual control adjustments. Commercially available. | The spectrometer is placed next to the tabletting press. During the tabletting process are samples removed, analysed and the porosity determined. The operator can adjust the tabletting press to optimize the porosity during manufacturing. |
| In-line, full spectrum | The NIR spectrometer is attached to the tabletting press. A robotic arm removes samples and places them in the NIR spectrometer for analysis. Analysis time ~30 seconds/tablet. Commercially available. | The spectrometer pc is interfaced with the tabletting press and signals for adjustment of the tabletting press is transferred automatically to optimize the porosity during manufacturing |
| In-line, single wavenumber | The tablets pass a measuring point when leaving the tabletting press. A light emitting diode (LED) based instrument measures the NIR reflectance at one specific wavelength from the surface of the tablets as they pass the measuring point. Analysis time ~ milliseconds. Not commercially available. Needs to be designed. | The spectrometer pc is interfaced with the tabletting press and signals for adjustment of the tabletting press is transferred automatically to optimize the porosity during manufacturing |

Example 7: Dissolution of Tablets

Tablets were prepared from compositions B and C (hereafter referred to as Tablet batch B and Tablet batch C, respectively) as described in Example 1 and their dissolution profile was determined according to Assay (V) as described herein. The results are shown in Table 7.

TABLE 7

Dissolution profile

| Time | Tablet batch B | | Tablet batch C | |
|---|---|---|---|---|
| from test start (min) | Semaglutide (% (w/w) of 10 mg) | SNAC (% (w/w) of 300 mg) | Semaglutide (% (w/w) of 20 mg) | SNAC (% (w/w) of 600 mg) |
| 15 | 62 | 65 | 63 | 62 |
| 30 | 86 | 87 | 105 | 100 |
| 45 | 91 | 90 | 106 | 100 |
| 60 | 93 | 92 | 106 | 100 |

These results show that GLP-1 and SNAC are co-released in Tablet batch B and Tablet batch C.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

Example 8: In Vivo Location and Duration of Tablet Erosion

The in vivo location and duration of tablet erosion was investigated in a clinical study using gamma-scintigraphy. The study also assessed the pharmacokinetic parameters of oral semaglutide and SNAC. In order to employ gamma scintigraphy, a gamma emitting isotope was incorporated into formulation F (Table 1), where indium-111 (111In) was used to label a sodium polystyrene sulfonate resin, which was incorporated into the tablets.

Manufacturing Process

The manufacturing process was a three-stage process whereby simple blending was undertaken to prepare the SNAC/magnesium stearate blend, the Amberlite® resin was radiolabelled and the final tablet was compressed by individually weighing out the aforementioned components as well as the semaglutide granules.

The SNAC/magnesium stearate blend was prepared by manual volumetric doubling of the magnesium stearate with the SNAC granules, followed by blending using an inflated plastic bag. Magnesium stearate was pre-screened before use through a 355 µm sieve.

Before compression the lubricated SNAC blend, semaglutide granules and radiolabelled Amberlite® IRP-69A resin were individually weighed out for each tablet and manually mixed until visually uniform.

The radiolabelled tablets were compressed using a manual Carver Model C tablet press (L145) at a compression force of 6.7 kN (8.8 kN/cm2). Tablets were compressed with a 7.5×13 mm radial oval convex tablet tooling. The tablet thickness was 6.4 mm. Hardness varied from 91-104 N, and bulk density was 1.07 g/cm$^3$ Dosing 24 Subjects were treated in a cross-over trial design so that all subjects received one period with dosing of 10 mg semaglutide and 50 ml water and one period with dosing of 10 mg semaglutide and 240 mL water. Dosing was performed with the subjects positioned in a sitting position in front of the gamma camera to provide an anterior view and permit measurement of oesophageal transit. Blood samples for pharmacokinetic profiles were collected and the pharmacokinetic assessments included 24-hours semaglutide profiles and 6-hours SNAC profiles. Scintigraphy dynamic imaging was performed (until 4 hour post-dosing) and safety and tolerability was assessed. The dynamic imaging was performed with the subjects sitting. Subjects remained in the camera room until completion of the rapid imaging phase (30 minutes post-dose). Static imaging was performed with subjects standing. Thereafter, subjects were permitted to leave the camera room. Subjects were permitted to sit or remain moderately active (walk around the clinical unit) and imaging continued until 4 hours post dosing. Initial tablet erosion (ITE) was defined as the first sign of sustained release of radioactive marker from the tablet. Complete tablet erosion (CTE) was defined as the time at which the entire radioactive marker had dispersed into the gastrointestinal tract and no signs of a distinct 'core' remain. The anatomical location of the capsule at the time of each event (ITE and CTE) was determined. Quantitative assessment of tablet erosion was performed to generate the tablet erosion time profile. A region of interest was drawn around the tablet and amount of radioactive marker retained within that region was quantified. Data was corrected for depth of radioactivity in the body, radioactive decay and background.

Blood samples were collected at −30, 0, 10, 20, 30, 40, 50 minutes, 1, 1.5, 2, 3, 4, 6 12 and 24 hours post dosing. Bioanalysis of semaglutide was performed using a validated assay and bioanalysis of SNAC was performed using a liquid chromatography mass spectrometry (LC/MS/MS) assay.

TABLE 8

Tablet erosion of tablets after dosing with 50 or 240 ml water

|  | 50 ml*) | 240 ml*) |
| --- | --- | --- |
| Time (min) to initial tablet erosion (SD) (min post-dose) | 6.0 (7.7) | 9.7 (18.4) |
| Time (min) to complete tablet erosion (SD) | 95.4 (49.4) | 66.2 (48.8) |
| Duration (min) of tablet erosion (SD) | 89.9 (48.8) | 56.4 (43.1) |

*)Standard deviation shown in brackets

The anatomical location of ITE and CTE was the stomach for all subjects, for both volumes of water tested. The duration of tablet erosion was to some degree influenced by water volume, however even with a large volume of water the duration of tablet erosion was surprisingly long (56±43 minutes). The long erosion time is a central aspect of the tablet technology.

Figure 5:
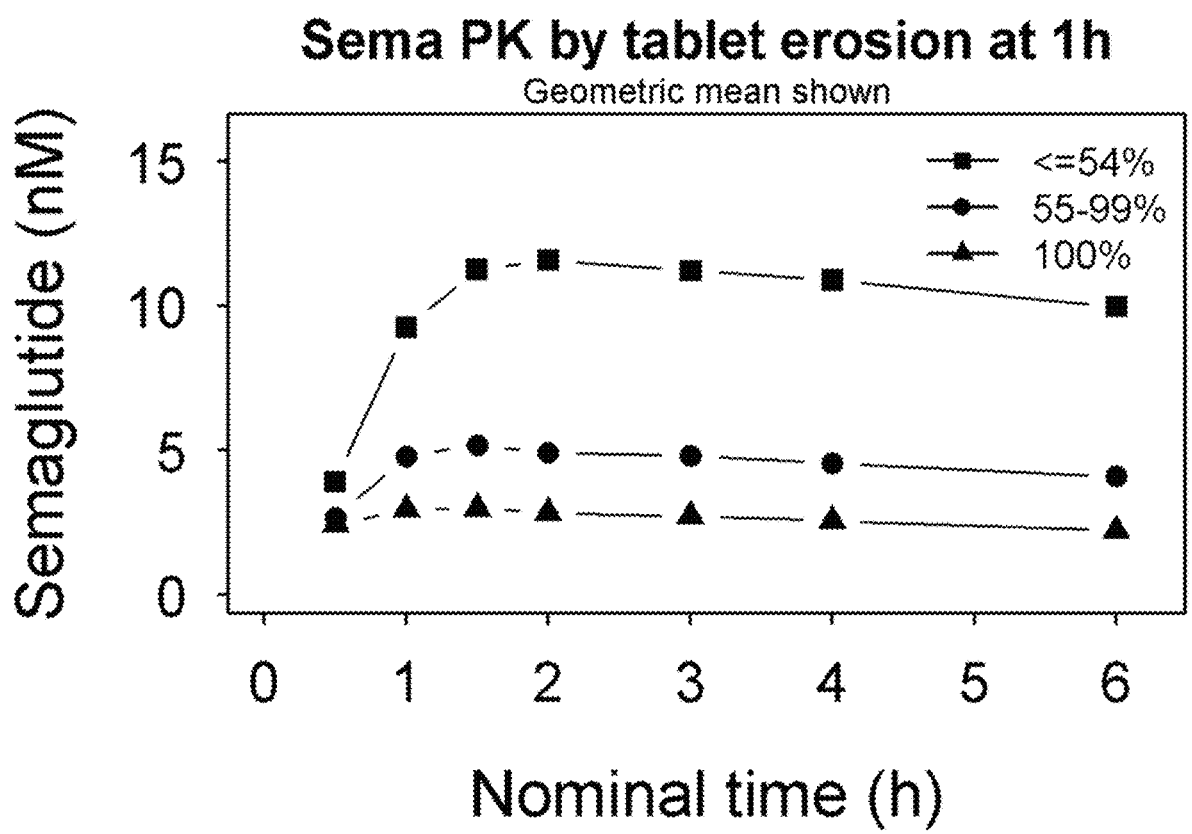
FIG. 5 shows correlation of semaglutide PK profiles with tablet erosion at 1 hour after dosing. <=54% tablet erosion at 1 hour (■), 55-99% erosion at 1 hour (●), 100% erosion at 1 hour (▲).

A negative correlation between tablet erosion at 1 hour post dosing and semaglutide plasma exposure is shown in FIG. 5. Full tablet erosion at 1 hour resulted in very low plasma exposure of semaglutide, whereas less than 54% tablet erosion resulted in high plasma exposure of semaglutide. It is seen that slow tablet erosion correlated with higher plasma semaglutide exposure and longer tmax of semaglutide.

Figure 6:
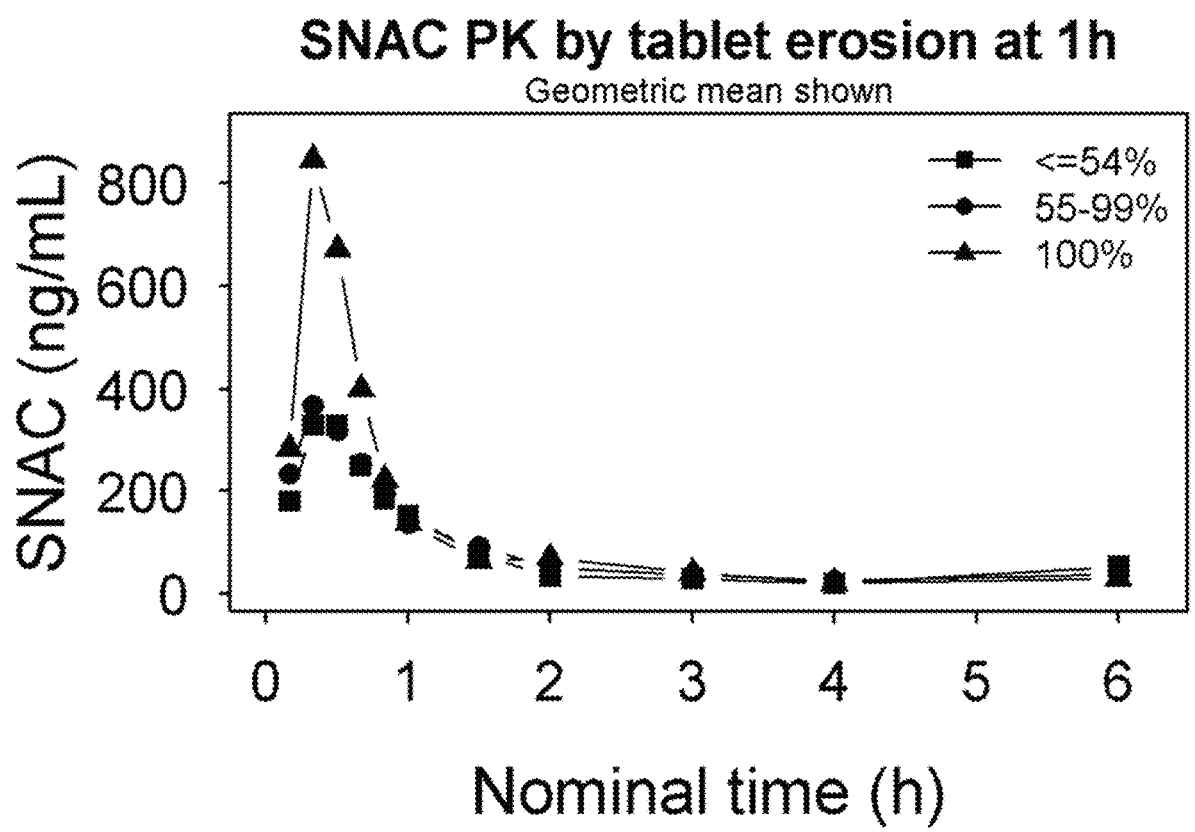
FIG. 6 shows correlation of SNAC PK profiles with tablet erosion at 1 hour after dosing. <=54% erosion at 1 hour (■), 55-99% erosion at 1 hour (●), 100% erosion at 1 hour (▲).

FIG. 6 shows that a higher degree of tablet erosion for a tablet containing 300 mg SNAC at 1 hour after dosing correlated with higher peak exposure to SNAC. Hence, plasma exposure and Cmax of SNAC correlated negatively with the efficacy of the tablet.

The invention claimed is:

1. A tablet comprising a granulate, wherein said granulate comprises: i) no more than 15% (w/w) GLP-1 peptide, wherein the GLP-1 peptide is a peptide; and ii) at least 50% (w/w) salt of N-(8-(2-hydroxybenzoyl)amino)caprylic acid (NAC); wherein said tablet has
   a) a bulk density of at least 1.0 g/cm³;
   b) a median pore diameter of no more than 1.5 µm; and
   c) a feature selected from the group consisting of a maximum pore diameter of no more than 4 µm, a crushing strength of 50-400 N, and a disintegration time of 22 minutes or less.

2. The tablet according to claim 1, wherein the GLP-1 peptide comprises a substituent comprising a fatty acid or a fatty diacid, of formula (X)

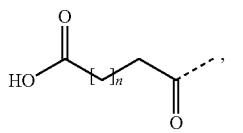

wherein n is at least 13;
and wherein said peptide optionally comprises one or more 8-amino-3,6-dioxaoctanoic acid (OEG).

3. The tablet according to claim 1, wherein the GLP-1 peptide is semaglutide.

4. The tablet according to claim 1, wherein the salt of NAC is monosodium NAC (SNAC).

5. The tablet according to claim 1, wherein the amount of the salt of NAC is 50-90% (w/w).

6. The tablet according to claim 1, wherein the tablet comprises an intragranular and an extragranular part, and wherein the extragranular part comprises a lubricant.

7. The tablet according to claim 1, wherein the granulate comprises
   i) 1-15% (w/w) GLP-1 peptide,
   ii) 55-85% (w/w) salt of NAC, and
   iii) 1-20% (w/w) binder; and wherein the tablet further comprises 10-35% (w/w) filler and 0.5-3% (w/w) lubricant.

8. The tablet according to claim 1, wherein the tablet does not comprise a superdisintegrant.

9. The tablet according to claim 1, wherein the tablet is for oral administration.

10. The tablet according to claim 1, wherein the tablet is prepared by exerting a compression force in the range of 2-25 kN.

11. A method of treating type 2 diabetes or obesity comprising administering to a subject in need of such treatment a tablet according to claim 1.

12. The tablet according to claim 4, wherein the SNAC is anhydrous SNAC monosodium salt.

13. The tablet according to claim 6, wherein the extragranular part further comprises a filler.

14. The tablet according to claim 1, wherein said granulate comprises: i) no more than 15% (w/w) GLP-1 peptide, wherein the GLP-1 peptide is a peptide and ii) at least 50% (w/w) salt of N-(8-(2-hydroxybenzoyl)amino)caprylic acid (NAC); wherein said tablet has
   a) a bulk density of at least 1.0 g/cm³;
   b) a median pore diameter of no more than 1.5 µm; and
   c) a maximum pore diameter of no more than 4 µm.

15. The tablet according to claim 1, wherein said granulate comprises: i) no more than 15% (w/w) GLP-1 peptide, and ii) at least 50% (w/w) salt of N-(8-(2-hydroxybenzoyl)amino)caprylic acid (NAC); wherein said tablet has
   a) a bulk density of at least 1.0 g/cm³;
   b) a median pore diameter of no more than 1.5 µm; and
   c) a crushing strength of 50-400 N.

16. The tablet according to claim 1, wherein said granulate comprises: i) no more than 15% (w/w) GLP-1 peptide, and ii) at least 50% (w/w) salt of N-(8-(2-hydroxybenzoyl)amino)caprylic acid (NAC); wherein said tablet has
   a) a bulk density of at least 1.0 g/cm³;
   b) a median pore diameter of no more than 1.5 µm; and
   c) a disintegration time of 22 minutes or less.

* * * * *